United States Patent [19]

Perboni et al.

[11] Patent Number: 5,693,634
[45] Date of Patent: Dec. 2, 1997

[54] UREA DERIVATIVES FOR USE IN TREATING BACTERIAL INFECTIONS

[75] Inventors: Alcide Perboni; Giorgio Pentassuglia; Daniele Andreotti; John Alexander Winders, all of Verona, Italy

[73] Assignee: Glaxo Wellcome S.p.A., Verona, Italy

[21] Appl. No.: 635,976

[22] PCT Filed: Nov. 9, 1994

[86] PCT No.: PCT/EP94/03686

§ 371 Date: May 9, 1996

§ 102(e) Date: May 9, 1996

[87] PCT Pub. No.: WO95/13278

PCT Pub. Date: May 18, 1995

[30] Foreign Application Priority Data

Nov. 10, 1993 [GB] United Kingdom ............... 9323137

[51] Int. Cl.⁶ .................................................. A61K 31/395
[52] U.S. Cl. .................................. 514/210; 540/302
[58] Field of Search ............................ 540/302; 514/210

[56] References Cited

U.S. PATENT DOCUMENTS 5,459,260  10/1995  Sendai et al. ................... 540/302

FOREIGN PATENT DOCUMENTS

| 0 416 953 | 3/1991 | European Pat. Off. . |
| 0502464 | 2/1992 | European Pat. Off. . |
| 0 507 313 | 10/1992 | European Pat. Off. . |
| 92 15586 | 9/1992 | WIPO . |

*Primary Examiner*—Mukund J. Shah
*Assistant Examiner*—Michael Bucknum
*Attorney, Agent, or Firm*—Bacon & Thomas

[57] ABSTRACT

The present invention relates to compounds of formula (I)

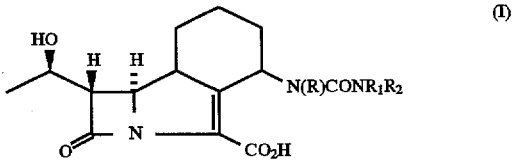

and salts and metabolically labile esters thereof. These compounds and compositions containing them have antibacterial activity. Processes for preparing these compounds are also disclosed, as well as methods of treatment of a human or non-human subject to combat bacterial infections.

16 Claims, No Drawings

UREA DERIVATIVES FOR USE IN TREATING BACTERIAL INFECTIONS

This application is a 371 of PCT/GP94/03686 dated Nov. 9, 1994.

This invention relates to urea derivatives having antibacterial activity, to processes for their preparation, to compositions containing them and to their use in medicine.

European Patent Application publication No. 0416953A2 describes 10-(1-hydroxyethyl)-11-oxo-1-azatricyclo[7.2.0.0$^{3,8}$]undec-2-ene-2-carboxylic acid and certain 4 substituted derivatives thereof, which have antibacterial activity.

European Patent Application publication No. 0422596A2 describes compound of the general formula

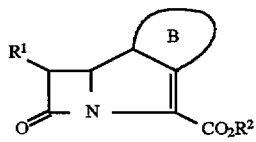

wherein $R^1$ is inter alia a 1-hydroxyethyl group, $CO_2R^2$ is a carboxy group which may optionally be esterified and ring B is a cyclic group which may be optionally substituted. Ring B may inter alia be a cyclohexane ring. The compounds have antibacterial activity. The specification specifically teaches compounds wherein B is an unsubsituted cyclohexane ring, but there is no teaching of specfic compounds wherein the cyclohexane ring is substituted.

European Patent Application No. 0507313A1 describes inter alia compounds of formula

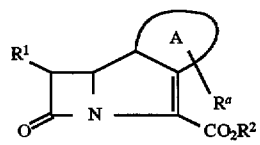

wherein $R^1$ is inter alia an optionally substituted lower alkyl group, $CO_2R^2$ is a carboxy group which may be esterified, ring A is inter alia a cyclohexane ring and $R^a$ is the group $W^aU^a$ [$W^a$ is a bond, sulphur (which may be in the form of mono- or dioxide), oxygen, NH (which may be substituted) or a straight-chain or branched lower alkylene or alkenylene group which may be interrupted by sulphur (which may be in the form of mono- or dioxide), oxygen or NH (which may be substituted); $U^a$ is carbamoyl, acyl which may be substituted, alkylammonium which may be substituted or a group of the formula

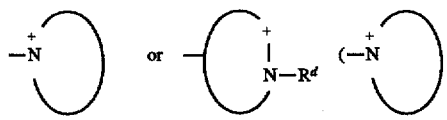

is a quaternized nitrogen-containing heterocyclic group which may be substituted and $R^d$ is an alkyl group which may be substituted)] which compounds have antibacterial activity. Preferred compounds of this class are said to be 10-(1-hydroxyethyl)-11-oxo-1-azatricyclo[7.2.0.0$^{3,8}$]undec-2-ene-2-carboxylic acid, derivatives wherein the group $R^a$ is $(CH_2)mK^a(CH_2)nU^a$ (wherein $K^a$ is $CH_2$, O, S or NH; m and n each is a whole number of 0 to 3; and $U^a$ is an N-linked quaternary ammonium group.

We have now discovered that the introduction of certain urea groupings at the 4 position of 10-(1-hydroxyethyl)-11-oxo-1-azatricyclo[7.2.0.0$^{3,8}$]undec-2-ene-2-carboxylic acid provides compounds with a particularly useful profile of activity as antibacterial agents.

According to the present invention, therefore we provide compounds of general formula (I)

salts and metabolically labile esters thereof;
wherein R represents hydrogen or $C_{1-6}$alkyl;
$R_1$ represents hydrogen or $C_{1-6}$alkyl;
$R_2$ represents hydrogen or an optionally substituted, alkyl, alkenyl, alkynyl, aryl, cycloalkyl or heterocyclic group.

In addition to the fixed stereochemical arrangement as defined in formula (I) the molecule contains a further asymmetric carbon atom at the 8-position, and another at the 4-position. It will be appreciated that all stereoisomers including mixtures thereof arising from these additional asymmetric centres, are within the scope of the compounds of formula (I). Compounds of formula (I) may also exist in tautomeric forms and such tautomers and derivatives thereof are also within the scope of the invention Salts of compounds of formula (I) include base addition salts for use in medicine such salts are formed with bases that have a physiologically acceptable cation. Suitable cations include those of alkali metals (e.g. sodium or potassium), alkaline earth metals (e.g. calcium), amino acids (e.g. lysine and arginine) and organic bases (e.g. procaine, phenylbenzylamine, dibenzylethylenediamine, ethanolamine, diethanolamine, and N-methyl glucosamine).

Salts derived from bases wherein the cation is not physiologically acceptable may be useful as intermediates for the preparation and/or isolation of other compounds of the invention, and these salts also form part of the invention.

When the group $R_2$ contains a basic centre, acid addition salts of such compounds and internal salts formed with the carboxylic acid grouping are also included in the invention.

It will be appreciated that the compounds of formula (I) may be produced in vivo by metabolism of a suitable metabolically labile ester. Examples of suitable metabolically labile esters include acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl or 3-phthalidyl.

The compound of formula (I) salts thereof and metabolically labile esters thereof may form solvates (e.g. hydrates) and the invention includes all such solvates. When R, $R_1$ and or $R_2$ are a $C_{1-6}$alkyl group they may be a straight or branched group e.g. methyl, ethyl, propyl, isopropyl, butyl, isobutyl, t-butyl, pentyl, isopentyl or hexyl.

When $R_2$ is alkenyl this is a $C_{3-6}$alkenyl group which may be a straight or branched chain group e.g. allyl, When $R_2$ is alkynyl this is a straight or branched chain $C_{3-6}$ alkynyl group e.g. propargyl.

When $R_2$ is a substituted alkyl, alkenyl or alkynyl group it is substituted by one or more substituents selected from optionally substituted aryl or aryloxy, azido halogen, hydroxy, cyano, nitro, trifluoromethyl, trifluoromethoxy, tri ($C_{1-4}$ alkyl ammonium, $C_{1-4}$alkoxy, $NR_3R_4$ (wherein $R_3$ and $R_4$ independently represent hydrogen or $C_{1-4}$alkyl), $NR_3R_8$ (wherein $R_8$ is acyl), $COR_5$ (wherein $R_5$ is hydroxy, $C_{1-4}$alkoxy or $NR_3R_4$), $CO_2R_6$ (wherein $R_6$ is $C_{1-4}$alkoxy or $NR_3R_4$) or $SO_2R_6$.

The term optionally substituted aryl as a group or part of group when used herein refers to a mono or bicyclic aryl group. Suitable monocyclic aryl groups include phenyl or a 5–6 membered heteroaryl group containing 1 to 3 heteroatoms selected from oxygen, sulphur or nitrogen. Examples of such heteroaryl groups include furanyl, thienyl, imidazolyl, thiazolyl, oxazolyl, pyrazolyl pyridinyl, pyridinium, pyridazinyl, pyrimidinyl or thiadiazolyl. Suitable bicyclo aryl groups contain 9 or 10 ring members selected from carbon, oxygen, sulphur and nitrogen with the proviso that at least 6 are carbon atoms.

Examples of such groups include naphthyl, indenyl, quinolinyl, benzofuranyl, benzimidazolyl, benzoxazolyl, indolyl, benzothiazolyl or phthalimidoyl.

When $R_2$ is a heteroaryl group it is attached to nitrogen atom of the urea group via a carbon atom member of the heteroaryl group.

When $R_2$ is or contains a substituted aryl group it is substituted by one or more groups selected from $C_{1-4}$alkyl, halogen, cyano, nitro, trifluoromethyl, trifluoromethoxy, succinimido or $(CH_2)nR_7$ wherein n is zero or an integer from 1 to 4 and $R_7$ is hydroxy, $C_{1-4}$alkoxy, $NR_3R_4$, $NR_3R_8$, $COR_5$, $CO_2R_6SO_2R_6$, or $S(O)_mR_9$ wherein m is zero 1 or 2 $R_9$ is $C_{1-4}$alkyl or $R_9$ is the group $NR_3R_4$ when m is 2.

When $R_2$ is an optionally substituted heterocyclic group this is a carbon linked 5–7 membered saturated heterocyclic group containing a single heteroatom selected from oxygen, sulphur or nitrogen. Examples of such groups include tetrahydropyranyl e.g. 4 tetrahydropyranyl or piperidinyl e.g. 4-piperidinyl and N-substituted derivative thereof e.g. N-alkyl or N-acyl derivatives.

When $R_2$ is optionally substituted cycloalkyl group it is a $C_{3-7}$ monocycloalkyl group such as cyclopropyl, cyclobutyl, cyclopentyl or cyclohexyl or cycloheptyl which may be substituted by one or more groups selected from $C_{1-4}$alkyl halogen, hydroxy, cyano, nitro, trifluoromethyl, trifluoromethoxy or $(CH_2)nR_7$.

When $R_8$ is acyl this may be for example $C_{1-6}$alkanoyl, aroyl e.g. benzoyl, or $C_{1-6}$alkoxycarbonyl The term halogen when used herein means fluorine, chlorine, bromine or iodine unless otherwise specified.

In a further aspect the invention provides compounds of formula (I) wherein R represents hydrogen or $C_{1-6}$methyl, $R_1$ represents hydrogen or $C_{1-6}$methyl, $R_2$ represents an optionally substituted alkyl, aryl, cycloalkyl or phenylalkyl group, The general formula (I) as drawn includes at least 4 stereoisomers and mixtures thereof and these may be represented by the formulae (1a, 1b, 1c and 1d).

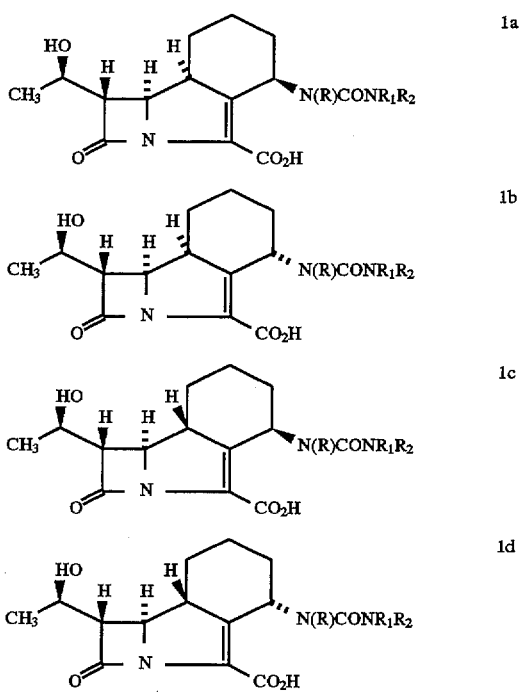

The solid wedge shaped bond indicates that the bond is above the plane of the paper. The broken bond indicates that the bond is below the plane of the paper.

When $R_2$ is an optionally substituted alkyl group conveniently this is a $C_{1-4}$alkyl group e.g. methyl, ethyl or t butyl optional substituted by a group selected from hydroxy, halo, azido, trimethylammonium, $COR_5$ wherein $R_5$ is OH, $C_{1-4}$alkoxy or $NR_3R_4$ (e.g. dimethylamino), $NR_3R_8$ (e.g. acetylamino, benzoylamino, or t-butoxycarbonylamino), optionally substituted phenyl, optionally substituted phenoxy, optionally substituted pyridyl or 1,2 oxazolyl. Examples of such $R_2$ groups include methyl, ethyl, t-butyl, ethyl (substituted by hydroxy, halo e.g. chlorine, azido, dimethylamino, trimethylammonium, carboxy, ethoxycarbonyl), $C_{1-2}$alkyl e.g. methyl or ethyl substituted by phenyl (optionally substituted by 1 or 2 groups selected from halogen e.g. chlorine or fluorine, or $SO_2NR_3R_4$), phenoxy, pyridyl, N-methyl pyridinium or 1,2 oxazolyl, When $R_2$ is an optionally substituted monocyclic aryl group this is conveniently a phenyl group [optionally substituted by 1 to 3 groups selected from $C_{1-4}$alkyl e.g. methyl or isopropyl, halo e.g. bromine, chlorine or fluorine, trifluoromethyl, nitro, cyano, hydroxy, alkoxy. e.g. methoxy, $COR_5$ e.g. $CO_2H$ or $CON(CH_3)_2$, $NHR_8$ (e.g. $CH_3CONH$), trimethylammonium, $S(O)_mCH_3$, $SO_2NR_3R_4$ e.g. $SO_2N(CH_3)_2$ or succinimido], pyridyl [optionally substituted by halogen e.g. chloride or bromine, trifluoromethyl, phenyl, hydroxy, alkoxy e.g., methoxy, oxo, or alkyl e.g. methyl], N-methylpyridinium, optionally substituted pyrimidinyl e.g. uracilyl, N-methyl uracilyl, N,N-dimethyl uracilyl or 2-thio uracilyl, optionally substituted furyl e.g. furyl or methyl furyl, optionally substituted thienyl e.g. thienyl or methylthienyl, pyrrole e.g. N-methylpyrrole, pyrazolyl or 1,5-dimethyl pyrazolyl or thiadiazolyl.

When $R_2$ is a heterocyclic group this is conveniently a 4-piperidinyl grouping optionally substituted on the nitrogen atom by or alkyl e.g. propyl, alkanoyl e.g. formyl or acetyl, or allyloxycarbonyl group; or a 4-tetrahydropyranyl group.

Examples of suitable R and $R_1$ groups include hydrogen or methyl

Examples of suitable $R_2$ groups include hydrogen, methyl, ethyl, t-butyl, allyl, propargyl, azidoethyl, hydroxyethyl, chloroethyl, dimethylaminoethyl, trimethylammonium-ethyl, 1-carboxyethyl, 2-ethoxycarbonylethyl, phenoxyethyl, benzamidomethyl, t butyxycarbonylaminomethyl, benzyl (optionally substituted by chloro and or fluoro, or by aminosulphonyl), phenylethyl, pyridylmethyl, pyridylethyl, N-methylpyridinium-methyl, 1,2 oxazolylmethyl, furfuryl, pyridyl, N-methylpyridinium, pyridyl (substituted by 1 or 2 chlorine or bromine atoms, trifluoromethyl, phenyl, or methoxy), N-methyl-2-pyridone, furyl, 2-methylfuryl, thienyl, methylthienyl, N-methylpyrrole, thiadiazolyl, methylthiadiazolyl, uracilyl, N-methyluracilyl, N,N-dimethyluracilyl, cyclohexyl, cyclopropyl, or 4-tetrahydropyranyl, or N-substituted 4-piperidinyl.

A preferred class of compounds of formula I are those in which the carbon atom at the 8-position is in the β configuration. Within this class those compounds in which the carbon atom at the 4-position is in the α configuration are particularly preferred.

A preferred class of compounds of formula (I) are those wherein R is methyl or hydrogen. A further preferred class of compounds of formula (I) are those wherein $R_1$ is hydrogen or methyl.

Compounds of formula (I) wherein one of the groups R, $R_1$ or $R_2$ has the meanings defined other than hydrogen represent a further preferred aspect of the invention.

Preferred $R_2$ groups include phenyl (optionally substituted by hydroxy, methoxy, cyano, acetamido or methylsulphonyl), pyridyl, pyridylmethyl, phenoxyethyl, furfuryl or uracilyl.

A preferred group of compounds of formula (I) include those wherein R and $R_1$ are hydrogen. Within this group those wherein $R_2$ is phenyl (optionally substituted by hydroxy, methoxy, cyano, acetamido, methylsulphonyl), pyridyl, pyridylmethyl, phenoxyethyl, furanyl or uracilyl are particularly preferred.

Specifically preferred compounds according to the invention include (4S,8S,9R,10S,12R)-4-(phenylaminocarbonylamino)-10-(1'-hydroxyethyl)-11-oxo-1-azatricyclo[7.2.0.0$^{3.8}$]-undec-2-ene-2-carboxylic acid;

(4S,8S,9R,10S,12R)-4-(3"-pyridineaminocarbonylamino)-10-(1'-hydroxyethyl)-11-oxo-1-azatricyclo[7.2.0.0$^{3.8}$]-undec-2-ene-2-carboxylic acid;

(4S,8S,9R,10S,12R)-4-[(2"-hydroxyphenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(4"-methylsuphonylphenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-(uracil-5'-amino)carbonilamino-10-(1'-hydroxyethyl)-11-oxo-1-aza-tricyclo[7.2.0.0$^{3,8}$]-undec-2-ene carboxylic acid;

(4S,8S,9R,10S,12R)-4-(3"-picolylaminocarbonylamino)-10-(1'-hydroxyethyl)-11-oxo-1-azatricyclo[7.2.0.0$^{3.8}$]-undec-2-ene-2-carboxylic acid;

(4S,8S,9R,10S,12R)-4-(2"-furfurylaminocarbonylamino)-10-(1'-hydroxyethyl)-11-oxo-1-azatricyclo[7.2.0.0$^{3.8}$]-undec-2-ene-2-carboxylic acid;

(4S,8S,9R,10S,12R)-4-[(2"-methoxyphenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(benzylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(3"-cyanophenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(2"-phenoxyethylaminocarbonyl)amino]-10-(1'-hydroxyethyl)-11-oxo-1-azatricyclo[7,2,0,0$^{3,8}$]-undec,-2-ene-2-carboxylic acid;

(4S,8S,9R,10S,12R)-4-[(4"-acetamidophenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(4"-cyanophenylaminocarbonyl)amino]-10-(1'-hydroxyethyl)-11-oxo-1-azatricyclo[7,2,0,0$^{3,8}$]-undec-2-ene-2-carboxylic acid and physiologically acceptable salt or metabolically labile ester thereof.

A further preferred compound of the invention is (4S,8S,9R,10S,12R)-4-(aminocarbonyl-N-methylamino)-10-(1'hydroxyethyl)-11-oxo-1-azatricyclo[7.2.0.0$^{3,8}$]-undec-2ene-2-carboxylic acid and physiologically acceptable salt or metabolically labile ester thereof Compounds according to the invention not only exhibit a broad spectrum of antibacterial activity against a wide range of pathogenic microorganisms but also have a very high resistance to all β-lactamases. Compounds of the invention are also relatively stable to renal dehydropeptidase.

Thus using a standard microtiter broth serial dilution test compounds of the invention have been found to exhibit useful levels of activity against a wide range of pathogenic microorganisims including strains of *Staphylococcus aureus, Streptococcus faecalis, Escherichia coli, Pseudomonas aeruginosa*, Klebisiella, pneumoniae, *Proteus microbilus, Clostridium perfringens* and *Bacteriodes fragilis*.

Compounds of the invention have also been found to exhibit a particularly advantageous serum half life in mice.

The compounds of the invention may therefore be used for treating a variety of diseases caused by pathogenic bacteria in human beings and animals.

Thus, according to another aspect of the present invention, we provide a compound of formula (I) or a physiologically acceptable salt thereof for use in the therapy or prophylaxis of systemic or topical bacterial infections in a human or animal subject.

According to a further aspect of the invention we provide the use of a compound of formula (I) or a physiologically acceptable salt thereof for the manufacture of a therapeutic agent for the treatment of systemic or topical bacterial infections in a human or animal body.

According to a yet further aspect of the invention we provide a method of treatment of the human or non-human animal body to combat bacterial infections which method comprises administering to the body an effective amount of a compound of formula (I) or a physiologically acceptable salt thereof.

While it is possible that, for use in therapy, a compound of the invention may be administered as the raw chemical it is preferable to present the active ingredient as a pharmaceutical formulation.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01–99% of the active material. For topical administration, for example, the composition will generally contain from 0.01–10%, more preferably 0.01–1% of the active material.

For systemic administration the daily dose as employed for adult human treatment will range from 5–100 mg/kg body weight, preferably 10–60 mg/kg body weight, which may be administered in 1 to 4 daily doses, for example, depending on the route of administration and the condition of the patient. When the composition comprises dosage units, each unit will preferably contain 200 mg to 1 g of active ingredient.

The duration of treatment will be dictated by the rate of response rather than by arbitrary numbers of days.

The compounds of formula (I) may be prepared from the compounds of formula (11) wherein R is as defined in formula (I) and $R_{10}$ is a hydrogen atom or a hydroxyl protecting group and $R_{11}$ is hydrogen or a carboxyl protecting group and $R_{12}$ is an optionally substituted phenoxy or imidazolyl group or halogen atom

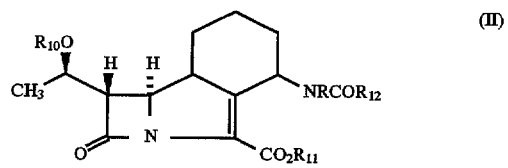

(II)

by reaction with an amine (III; $R_1R_2NH$) wherein $R_1$ and $R_2$ have the meanings defined above, followed where necessary or desired by removal of the hydroxyl protecting group $R_{10}$ and the carboxy protecting group $R_{11}$. The reaction is preferably carried out in a solvent such as a halohydrocarbon (e.g. dichloromethane) or an ether (e.g. tetrahydrofuran) or an amide (e.g. N,N-dimethylformamide) or acetonitrile at a temperature with the range of room temperature to the reflux temperature of the solvent and optionally in the presence of a base such as a tertiary amine e.g. triethylamine.

In a further process of the invention compounds of formula (I) may be prepared by reaction of the amine (IV) in which R has the meanings defined in formula (I) and $R_{10}$ and $R_{11}$ are as defined in formula (II)

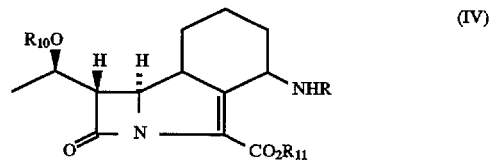

(IV)

$R_2NCO$ (V)

$R_1R_2NCOR_{12}$ (VI)

with the isocyanate (V) wherein $R_2$ has the meanings defined in formula (I) or is a protected derivatives thereof, or the compound (VI) wherein $R_1$ and $R_2$ have the meanings defined or are a protected derivative thereof and $R_{12}$ is an optionally substituted phenoxy or imidazolyl group or halogen followed where necessary or desired by removal of any protecting group.

The reaction with the isocyanate (V) is conveniently carried out in a solvent such as tetrahydrofuran or aqueous tetrahydrofuran, a halohydrocarbon (e.g. dichloromethane), or acetonitrile optionally in the the presence of a base such as triethylamine, and at a temperature with the range of 0°–80° C.

The reaction with the compound (VI) is preferably carried out in a solvent such as a halohydrocarbon (e.g. dichloromethane) or an ether (e.g. tetrahydrofuran) or an amide (e.g. N,N-dimethylformamide) at a temperature with the range of room temperature to the reflux temperature of the solvent and optionally in the presence of a base such as a tertiary amine e.g. triethylamine. When the reaction is carried out using a compound of formula (VI) wherein $R_{12}$ is halogen the reaction is conveniently carried out at a temperature with the range 0–60.

The compounds of formula I wherein R and $R_1$ are $C_{1-6}$ alkyl may be obtained by the cyclisation of a compound of formula (VII)

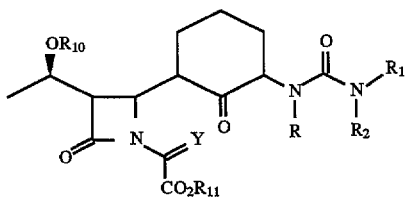

Wherein R, $R_1$ and $R_2$ have the meaning defined in formula I or are a protected derivatives thereof with the proviso that $R_1$ and or R are not hydrogen, $R_{10}$ and $R_{11}$ are as defined in formula (11), Y is an oxygen atom or a phosphine group, and if required or desired subjecting the resulting compound prior to or subsequent to any separation into its stereochemical isomers, to one or more of the following operations:

a) removal of one or more protecting groups b) conversion of a compound in which $R_{11}$ is hydrogen or a carboxyl protecting group into a salt of an inorganic or organic base, an acid addition salt thereof or a metabolically labile ester thereof.

The cyclisation of a compound of formula (VII) in which Y is oxygen is conveniently carried out by heating in the presence of an organic phosphite.

The reaction is preferably carried out in a solvent or mixture of solvents at a temperature within the range 60°–200°.

Suitable solvents include hydrocarbons with an appropriate boiling point, for example aromatic hydrocarbons, such as toluene or xylene.

Suitable organic phosphites include acyclic and cyclic trialkylphosphites, triarylphosphites and mixed alkylarylphosphites. Particularly useful organic phosphites are the trialkylphosphites e.g. triethylphosphite or trimethylphosphite.

The cyclisation of a compound of formula (VII) in which Y is a phosphine grouping is preferably carried out in a solvent at a temperature between 40°–200° C. Suitable solvents include hydrocarbons such as aromatic hydrocarbons, for example xylene or toluene, aliphatic hydrocarbons and halogenated hydrocarbons such as dichloromethane, chloroform and trichloroethane. Examples of suitable phosphine groups are triarylphosphines e.g. triphenyl phosphine or trialkylphospines e.g. tri-t-butylphospine.

The hydroxyl and carboxyl protecting groups $R_{10}$ and $R_{11}$ may be removed by conventional procedures and in any order. More preferably however the hydroxyl protecting group $R_{10}$ is removed prior to the removal of the carboxyl protecting group. Such removal of the protecting groups is a further feature of the invention.

The hydroxyl protecting groups may be removed by well known standard procedures such as those described in Protective Groups in Organic Chemistry, pages 46–119, edited by J. F. W. Mc Omie (Plenum Press, 1973). For example when $R_{10}$ is a t-butyldimethylsilyl group, this may be removed by treatment with tetrabutylammonium fluoride and acetic acid. This process is conveniently carried out in a solvent such as tetrahydrofuran. Similarly when $R_{10}$ is a 4-nitrobenzyloxycarbonyloxy group this may be removed by treatment with hydrogen and a metal catalyst e.g. palladium on carbon.

The carboxyl protecting group $R_{11}$ may also be removed by standard processes such as those described in Protective Groups in Organic Chemistry, pages 192–210, edited by J. F. W. Mc Omie (Plenum Press 1973). For example when $R_{11}$ represents an arylmethyl group this may be removed by conventional procedures using hydrogen and a metal catalyst e.g. palladium. When the group $R_{11}$ represents an allyl or substituted allyl group then this is preferably removed by treatment with an allyl acceptor in the presence of tetrakis (triphenylphosphine)palladium and optionally in the presence of triphenylphospine. Suitable allyl acceptors include sterically hindered amines such as tertbuylamine, cyclic secondary amines such as morpholine or thiomorphonine, tertiary amines such as triethylamine, aliphatic or cycloapliphatic β-dicarbonyl compounds such as acetylacetone, ethyl acetoacetate or dimedone, an alkanoic acids or alkali metal salts thereof such as acetic acid, propionic acid or 2-ethyl hexanoic acid or the potassium or sodium salt thereof, or 5,5-dimethyl-1,3-cyclohexadiene.

A particularly useful allyl acceptor is 5,5-dimethyl 1,3-cyclohexadiene.

The reaction is preferably carried out in an inert solvent such as an ether e.g. diethyl ether or tetrahydrofuran, an alkanol e.g. ethanol, an ester e.g. ethyl acetate or a halohydrocarbon e.g. methylene chloride, or mixtures thereof. The reaction is conveniently carried out in the temperature range 0°–40° more particularly at room temperature.

Compounds of the invention in which the group $R_{11}$ is a physiologically acceptable cation may be prepared from compounds of the invention in which $R_{11}$ is hydrogen by treatment with a suitable base. Conveniently the salt is formed in solution and then if required precipitated by the addition of a non-solvent e.g. a non polar aprotic solvent. Alternatively the sodium or potassium salt may be prepared by treating a solution of a compound of formula (II) in which $R_{11}$ represents a hydrogen atom with a solution of sodium or potassium 2-ethylhexanoate in a non-polar solvent such as diethyl ether.

Compounds of formula (IV) are either known or may be prepared according to the processes described in EPA No. 0416953A2 or WO 92/15586.

Compounds of formula (II) may also be prepared by analogous methods to those described in EPA No. 0416953A2 and WO 92/15586. Thus reaction of the epoxide (VIII)

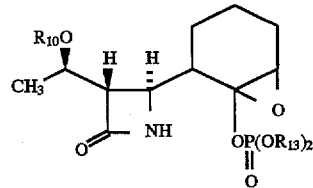

wherein $R_{10}$ is hydroxyl protecting group and $R_{13}$ is $C_{1-4}$alkyl, with ammonia or the amine $RNH_2$ wherein R is as defined in formula (I) gives the amino derivative (IX)

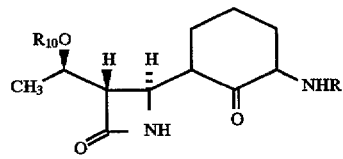

Reaction of the amino compound (VIII) with the appropriate chloroformate $R_{12}COCl$ wherein $R_{12}$ is an optionally substituted phenoxy group in the presence of a base such as pyridine, lutidine or triethylamine yields the corresponding carbamate(IX)

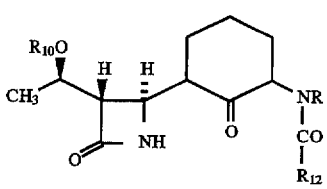
(X)

The compound (X) may be converted into the compound of formula (II) using the general procedures described in EPA NO. 0416953A2.

In the above reaction when it is necessary or desirable to use a hydroxyl protecting group $R_{10}$ suitable hydroxyl protecting groups include trialkylsilyl e.g. trimethylsilyl or t-butyldimethylsilyl,.

Suitable carboxyl protecting groups $R_{11}$ for use in the above reactions include arylmethyl groups such as benzyl, p-nitrobenzyl t-butylbenzyl or trityl, allyl or substitured allyl groups or trialkylsilylalkyl e.g. trimethylsilyl ethyl.

In the above processes for preparing the compounds of the invention via the compounds of formula (II) or (IV) it may also be necessary to protect reactive groups in the amine $R_1R_2NH$, or the isocyante $R_2NCO$. Thus if $R_2$ contains a primary or secondary amino group or a hydroxyl group it may be necessary to protect this group in a conventional manner e.g. as an, allyloxycarbonyl or a trimethylsilyl derivative thereof.

The various protecting groups may be removed in a conventional manner.

Compounds of formula (VII) in which Y=O may be prepared by treating a compound of formula (XI) in which the groups $R_{10}$, R, $R_1$, $R_2$ have the meanings given above with an activated derivative of the acid (XII) in which $R_{11}$ is a carboxyl protecting group.

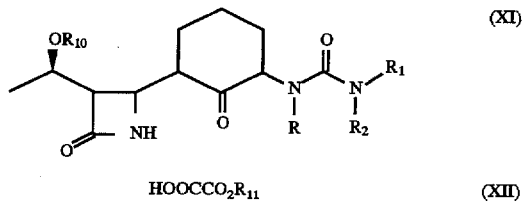
(XI)

HOOCCO$_2$R$_{11}$ (XII)

Suitable activated derivatives of the acid (XII) includes the corresponding acide halides e.g. acid chloride.

When the acid halide is used as the activated derivative of the acid (XII) then the reaction is preferably carried out in the presence of an acid acceptor such as a tertiary organic base for example pyridine or a trialkylamine in an aprotic solvent such as dichloromethane.

The compound of formula (VII) in which Y is a phosphine group may be prepared by treating the intermediate (XIII) in which L is a leaving group such as a halogen e.g. chlorine.

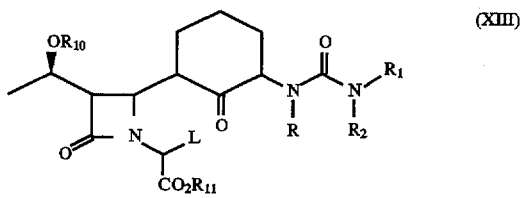
(XIII)

with the corresponding phosphine e.g. triphenylphosphine in the presence of a base. The reaction is conveniently carried out in a solvent such as dioxan in the presence of a tertiary organic base, e.g. 2,6 lutidine.

The compounds of formula (XIII) may be prepared form the corresponding hydroxy derivative (XIV) by conventional means for converting hydroxyl groups into leaving groups.

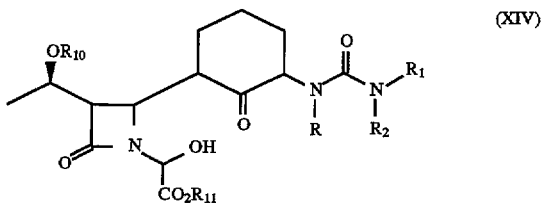
(XIV)

Thus for example a compound of formula (XIII) in which L is a chlorine atom may be prepared by treating a compound of formula (XIV) with thionyl chloride in an aprotic solvent such as dioxan or tetrahydrofuran and in the presence of a tertiary organic base e.g. 2,6-lutidine. Compounds of formula (XIV) may be prepared from the reaction of a compound of formula (XI) with glyoxylic ester (XV; $CHOCO_2R_{11}$) preferably in the form of its hydrate or hemiacetal. The reaction is preferably carried out in an aprotic solvent such as toluene and in the presence of an activated molecular sieve.

The compound of formula (XI) may be prepared by oxidation of compound of formula (XVI)

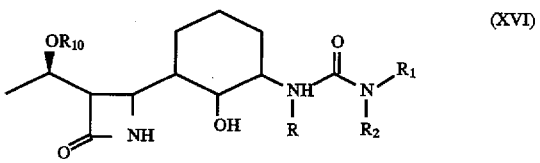
(XVI)

wherein $R_2$ is the meanings defined in formula (I) or is a protecting derivatives thereof, R and $R_1$ are $C_{1-6}$ alkyl group.

The oxidation may be carried out using conventional oxidising agents known in the art for converting a secondary alcohol such as cyclohexanol into a ketone such as cyclohexanone.

Thus for example the reaction may be carried out using oxalyl chloride and dimethylsulphoxide in a solvent such as methylene chloride. The compounds of formula. (XVI) may be prepared by reaction of compounds of formula (XVII) wherein $R_{10}$ is defined as in formula (X)

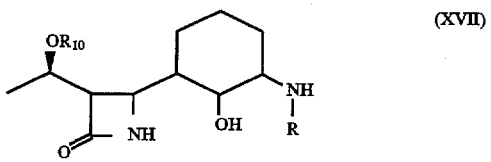
(XVII)

with carbamoyl chloride ClCONR1R2 where in the R1 is C1-6 alkyl and R2 is defined as in formula I Compounds of formula (XVII) are either known or may be prepared according to the processes describing in EPA No. 0416953A2 or WO 92/15586

In any of the formulae (I) to (XVII)) shown above when there is an asymmetric carbon atom and no specific configuration is shown then the formula includes all possible configurations.

Specific stereoisomers of the compounds of formula (I) as defined in formulae 1a, 1b, 1c and 1d, essentially free of the other stereoisomers may be prepared by using the general processes described above starting with the appropriate stereoisomer of formula (II) or (IV).

The processes described above for preparing the compounds of formula (II) will in general give a mixture of stereoisomers.

The individual stereoisomers of the compounds of formula (II) may be prepared using the processes described above starting with the appropriate steroisomer of formula (V).

In order that the invention may be more fully understood the following examples are given by way of illustration only.

In the Preparations and Examples, unless otherwise stated:

Infrared spectra were measured in chloroform-$d_1$ solutions on a FT-IR instrument. Proton Magnetic Resonance (1H-NMR) spectra were recorded at 300 MHz gas solutions in $D_2O$. Chemical shifts are reported in ppm downfield ($\delta$) from $Me_4Si$, used as an internal standard. Temperatures are in 0° C.

Intermediate 1

Benzyl-(4S,8S,9R,10S,12R)-4-[(N-allyloxycarbonyl-N-methyl)amino]-10-(1'-t-butyldimethylsilyloxy)ethyl]-11-oxo-1-azatricyclo[7.2.0.0$^{3,8}$]undec-2-ene-2-carboxylate To a solution of (3S,4R)-3-[R-1-(t-butyldimethylsilyloxy)ethyl]-4-[(2'S,6'R)-2'-(N-allyloxycarbonyl-N-methylamino-1'-oxocyclohex-6-yl)]azetidin-2-one (12 g) in anhydrous methylene chloride (120 ml) potassium carbonate (7.5 g) and pyridine (5.9 ml) were added under nitrogen atmosphere. The mixture was cooled to 0° C., then a solution of benzyl oxalylchloride (10.9 g) in anhydrous methylene chloride (30 ml) was dropped. After 3 hrs the mixture was poured into a cold satured sodium hydrogen carbonate solution (100 ml) and then extracted with ethyl acetate (250 ml). The organic layer was washed with a cold solution of ammonium chloride (100 ml) and brine (50 ml), then it was dried and evaporated under reduced pressure. The crude was purified by flash chromatography (eluant: cyclohexane/ethyl acetate 7:3) to give an oil (16 g) which was dissolved in nonane (300 ml). Triethylphosphite (27.8 ml) was added and the solution was refluxed overnight. After cooling to room temperature, 5% hydrogen peroxide solution (250 ml, 5% solution) was added, the mixture was stirred for 3 hrs then extracted with ethyl acetate (200 ml). The organic layer was washed with $H_2O$ (100 ml), brine (50 ml), then dried and evaporated under reduced pressure. After flash chromatography (eluant: cyclohexane/ethyl acetate 7:3) the title compound was obtained (10 g) as a yellow oil.

Intermediate 2

Benzyl-(4S,8S,9R,10S,12R)-4-methylamino-10-[(1'-t-butyldimethylsilyloxy)ethyl]-11-oxo-1-azatricyclo[7.2.0.0$^{3,8}$]undec-2-ene-2-carboxylate Intermediate 1 (2 g) was dissolved in anhydrous methylene chloride (25 ml) under nitrogen atmosphere and cooled to 0° C. N,N-dimethyltrimethylsilylamine (1.7 ml), trimethylsilyl trifluoroacetate (1.8 ml) and a suspension of palladium tetrakis(triphenylphosphine) (0.200 g) in anhydrous methylene chloride (1 ml) were added. After 15 min. the mixture was poured into a satured sodium hydrogen carbonate solution (20 ml) and extracted with ethyl acetate (100 ml). The organic layer was dried and evaporated under reduced pressure. The crude was purified by flash chromatography (eluant ethyl acetate) to give the title compound (1.2 g) as a yellow oil.

Intermediate 3

Benzyl-(4S,8S,9R,10S,12R)-4-[(N-chlorocarbonyl-N-methyl)amino]-10-[(1'-t-butyldimethylsilyloxy)ethyl]-11-oxo-1-azatricyclo[7.2.0.0$^{3,8}$]undec-2-ene-2-carboxylate A solution of intermediate 2 (0.500 g) in anhydrous methylene chloride (10 ml) under nitrogen atmosphere was cooled to −50° C., then a solution of phosgene (0.75 ml of a solution 1.93M in toluene) and triethylamine (0.440 ml) in anhydrous methylene chloride (4 ml) was dropped. After 2 hrs at −50° C. the reaction was quenched with a cold satured sodium hydrogen carbonate solution (20 ml) and extracted with ethyl acetate (50 ml). The organic layer was dried and evaporated under reduced pressure. After flash chromatography (eluant: cyclohexane/ethyl acetate 7:3) the title compound was obtained (0.430 g) as a yellow oil.

Intermediate 4

Benzyl-(4S,8S,9R,10S,12R)-4-[N-[(N-benzyl-N-methyl)aminocarbonyl]-N-methyl]amino-10-[(1'-t-butyldimethylsilyloxy)ethyl]-11-oxo-1-azatricyclo[7.2.0.0$^{3,8}$]undec-2-ene-2carboxylate To a solution of intermediate 2 (0.400 g) in anhydrous toluene (20 ml) triethylamine (0.160 ml) and benzylmethylcarbamoyl chloride (0.395 g) were added. The mixture was warmed to 80° C. for 24 hrs, then poured into a satured ammonium chloride solution (50 ml) and extracted with ethyl acetate (100 ml). The organic layer was washed with a satured sodium hydrogen carbonate solution (50 ml) and brine (50 ml), then dried and evaporated under reduced pressure. The crude was purified by flash chromatography (eluant: cyclohexane/ethyl acetate 7:3) to give the title compound (0.120 g) as a yellow oil.

Intermediate 5

Benzyl-(4S,8S,9R,10S,12R)-4-[N-[(N-benzyl-N-methyl)aminocarbonyl]-N-methyl]amino-10-(1'-hydroxyethyl)-11-oxo-1-azatricyclo[7.2.0.0$^{3,8}$]undec-2-ene-2-carboxylate To a solution of intermediate 4 (0.340 g) in anhydrous tetrahydrofuran (20 ml) acetic acid (0.185 ml) and tetrabutylammonium fluoride (2.16 ml of a 1M solution in tetrahydrofuran) were added. The solution was stirred at room temperature for 4 days, then diluted with ethyl acetate (150 ml) and washed with a satured sodium hydrogen carbonate solution (50 ml) and brine (50 ml). The organic layer was dried and evaporated under reduced pressure. The crude was purified by flash chromatography (eluant: cyclohexane/ethyl acetate 1:1) to give the title compound (0.225 g) as a white solid.

Intermediate 6

Benzyl-(4S,8S,9R,10S,12R)-4-[N-[N-(2-pyridyl)-N-methylaminocarbonyl]-N-methyl]amino-10-[(1'-t-butyldimethylsilyloxy)ethyl]-11-oxo-1-azatricyclo[7.2.0.0$^{3,8}$]undec-2-ene-2-carboxylate To a solution of intermediate 2 (0.300 g) in anhydrous toluene (20 ml) triethylamine (0.340 ml) and 2-pyridylmethylcarbamoyl chloride (0.210 g) were added. The mixture was warmed to 40° C. for 7 hrs and at room temperature over night, then poured into a satured ammonium chloride solution (50 ml) and extracted with ethyl acetate (100 ml). The organic layer was washed with a satured sodium hydrogen carbonate solution (50 ml) and brine (50 ml), then dried and evaporated under reduced pressure. The crude was purified by flash chromatography (eluant: cyclohexane/ethyl acetate 1:1) to give the title compound (0.240 g) as a yellow oil.

Intermediate 7

Benzyl-(4S,8S,9R,10S,12R)-4-[N-[N-(2-pyridyl)-N-methylaminocarbonyl]-N'-methyl]amino-10-(1'-hydroxyethyl)-11-oxo-1-azatricyclo[7.2.0.0$^{3,8}$]undec-2-ene-2-carboxylate To a solution of intermediate 6 (0.230 g) in anhydrous tetrahydrofuran (20 ml) acetic acid (0.130 ml) and tetrabutylammonium fluoride (0.470 g in 2 ml of tetrahydrofuran) were added. The solution was stirred at room temperature for 4 days, then diluted with ethyl acetate (150 ml) and washed with a satured sodium hydrogen carbonate solution (50 ml) and brine (50 ml). The organic layer was dried and evaporated under reduced pressure. The crude was purified by flash chromatography (eluant: ethyl acetate) to give the title compound (0.110 g) as a white solid.

IR (CDCl$_3$) V$_{max}$ cm$^{-1}$: 3408, 1717.

Intermediate 8

Benzyl-(4S,8S,9R,10S,12R)-4-[N-[N-2-(2-pyridylethyl)-N'-methylaminocarbonyl]-N-methyl]amino-10-[(1'-t-butyldimethylsilyloxy)ethyl]-11-oxo-1-azatricyclo[7.2.0.0$^{8,3}$]undec-2-ene-2-carboxylate To a solution of intermediate 3 (0.180 g) in anhydrous methylene chloride (10 ml) triethylamine (0.045 ml) and 2-(2-methylaminoethyl)pyridine (0.045 ml) were added. The mixture was stirred overnight at room temperature then quenched with a satured ammonium chloride solution (10 ml) and extracted with ethyl acetate (50 ml). The organic layer was dried and evaporated under reduced pressure. The crude was purified by flash chromatography (eluant: cyclohexane/ethyl acetate 2:8) to give the title compound (0.200 g) as a yellow oil.

Intermediate 9

Benzyl-(4S,8S,9R,10S,12R)-4-[N-[N-2-(2-pyridylethyl)-N-methylaminocarbonyl]-N'-methyl]amino-10-(1'-hydroxyethyl)-11-oxo-1-azatricyclo[7.2.0.0$^{3,8}$]undec-2-ene-2-carboxylate To a solution of intermediate 8 (0.195 g) in anhydrous tetrahydrofuran (20 ml) acetic acid (0.105 ml) and tetrabutylammonium fluoride (0.370 g in 2 ml of tetrahydrofuran) were added. The solution was stirred at room temperature for 4 days, then diluted with ethyl acetate (150 ml) and washed with a satured sodium hydrogen carbonate solution (50 ml) and brine (50 ml). The organic layer was dried and evaporated under reduced pressure. The crude was purified by flash chromatography (eluant: ethyl acetate) to give the title compound (0.120 g) as a white solid.

$^1$H-NMR (300 MHz, CDCl$_3$): 8.52 (d), 7.59 (td), 7.45 (d), 7.40–7.10 (m), 5.37 (d), 5.22 (d), 5.01 (t), 4.24 (m), 4.09 (dd), 3.66 (m), 3.18 (dd), 3.04 (t+m), 2.90 (s), 2.48 (s), 2.30–1.20 (m), 1.33 (d).

MS (VGquattro-FAB-NBA) m/z: 533.

Intermediate 10

Benzyl-(4S,8S,9R,10S,12R) 4-[(N-allyloxycarbonyl-N-methyl)amino]-10-(1'-hydroxyethyl)-11-oxo-1-azatricyclo[7.2.0.0$^{3,8}$]undec-2-ene-2-carboxylate Acetic acid (3.32 ml) and tetrabutylammonium fluoride trihydrate (12.2 g) were added to a solution of intermediate 1 (5.5 g) in distilled tetrahydrofuran (250 ml) under a nitrogen atmosphere. The resulting solution was stirred at 23° for 18 h, then diluted with ethyl acetate (500 ml) and washed with a satured sodium hydrogen carbonate solution (400 ml) and brine (400 ml). The organic layer was dried (Na$_2$SO$_4$) and concentrated in vacuo to an oil which was purified by flash chromatography, eluting with cyclohexane/ethyl acetate 3:7, to give the title compound (2.6 g) as a pale yellow oil.

IR (CDCl$_3$) V$_{max}$ cm$^{-1}$: 1774, 1720 and 1691 (C=O)

Intermediate 11

Benzyl-(4S,8S,9R,10S,12R) 4-[(N-allyloxycarbonyl-N-methyl)amino]-10-[1'-(4-nitrobenzyloxycarbonyl)hydroxyethyl]-11-oxo-1-azatricyclo[7.2.0.0$^{3,8}$]undec-2-ene-2-carboxylate 4-Dimethylaminopyridine (184 mg) and 4-nitrobenzylchloroformiate (296 mg) were added to a solution of intermediate 10 (640 mg) in dry dichloromethane (35 ml) under a nitrogen atmosphere. The solution was stirred at 23° for 1 h, then further 4-dimethylaminopyridine (368 mg) and 4-nitrobenzylchloroformiate (592 mg) were added. The reaction mixture was stirred at 23° for 1 h, then diluted with ethyl acetate (100 ml) and washed with satured ammonium chloride solution (70 ml), satured sodium hydrogen carbonate solution (70 ml) and brine (70 ml). The organic layer was dried (Na$_2$SO$_4$) and concentrated in vacuo to an oil, which was purified by flash chromatography, eluting with cyclohexane/ethyl acetate 6:4, to give the title compound (700 mg) as a white foam.

IR (CDCl$_3$) V$_{max}$ cm$^{-1}$: 1774, 1749 and 1713 (C=O)

Intermediate 12

Benzyl (4S,8S,9R,10S,12S) 4-methylamino-10-[1'-(4-nitrobenzyloxycarbonyl)hydroxyethyl]-11-oxo-1-azatricyclo[7.2.0.0$^{3,8}$]undec-2-ene-2-carboxylate A solution of intermediate 11 (700 mg) in dry dichloromethane (8 ml) was cooled to 0°, then N,N-dimethyltrimethylsilylamine (0.52 ml), trimethylsilyl trifluoroacetate (0.56 ml) and a suspension of palladium tetrakis triphenilphosphine (64 mg) in dry dichloromethane (1 ml) were added under a nitrogen atmosphere.

The mixture was stirred at 0° for 30 min, then diluted with ethyl acetate (20 ml) and washed with a satured sodium hydrogen carbonate solution (20 ml) and brine (20 ml). The organic phase was dried (Na$_2$SO$_4$) and concentrated in vacuo; the residue was purified by flash chromatography eluting with ethyl acetate/methanol 98:2 to give the title compound (360 mg) as a white foam.

Intermediate 13

Benzyl (4S,8S,9R,10S,12R) 4-[(N-chlorocarbonyl-N-methyl)amino]-10-[1'-(4-nitrobenzyloxycarbonyl)hydroxyethyl]-11-oxo-1-azatricyclo[7.2.0.0$^{3,8}$]undec-2-ene-2-carboxylate A solution of intermediate 12 (320 mg) and triethylamine (0.25 ml) in dry dichloromethane (5 ml) was added to a 1.93M solution of phosgene in toluene (0.47 ml) previously cooled to −78° under a nitrogen atmosphere. The resulting solution was stirred at −50° for 1 h, then diluted with ethyl acetate (15 ml) and washed with satured sodium hydroxide solution (15 ml) and brine (15 ml). The organic layer was dried (Na$_2$SO$_4$) and concentrated in vacuo; the residue was purified by flash chromatography, eluting with cyclohexane/ethyl acetate 4:6, to give the title compound (0.2 g) as a yellow oil.

IR (nujol) V$_{max}$ cm$^{-1}$: 1780 and 1734 (C=O)

Intermediate 14

Benzyl (4S,8S,9R,10S,12R) 4-{N-[(1"-S-benzyloxycarbonylethyl)carbamoyl]-(N-methyl)}amino-10-[1'-(4-nitrobenzyloxycarbonyl)hydroxyethyl]-11-oxo-1-azatricyclo[7.2.0.0$^{3,8}$]undec-2-ene-2-carboxylate Triethylamine (0.093 ml) and L-alanine benzyl ester (69 mg) were added to a solution of intermediate 13 (195 mg) in dry dichloromethane (5 ml) under a nitrogen atmosphere. The resulting mixture was stirred at 23° for 24 h, then diluted with ethyl acetate (20 ml) and washed with a satured ammonium chloride solution (20 ml) and brine (20 ml). The organic layer was dried ($Na_2SO_4$) and concentrated in vacuo; the residue was purified by flash chromatography, eluting with cyclohexane/ethyl acetate 2:8, to give the title compound (175 mg) as colourless oil.

IR ($CDCl_3$) $V_{max}$ $cm^{-1}$: 1745, 1645 (C=O); 1603 (C=C)

Intermediate 15

(3S,4R)-3-[(R)-1-(t-butydimethylsilyloxy)ethyl]-4-((R)-2'-((S)-6'-[N-[(N'-methyl-N'-phenyl)aminocarbonyl]-N-methylamino-1'-hydroxycyclohexyl]-azetidin-2-one To a solution of intermediate (3S,4R)-3-[R-1-(t-butyldimethylsilyloxy)ethyl]-4-[(,2'S,6'R)-2'-(N-allyloxycarbonyl-N-methylamino-1'-hydroxycyclohex-6-yl)]azetidin-2-one (1.437 g) in dichloromethane (55 ml) a room temperature triethylamine (0.90 ml) and N-methyl-N-phenylcarboxy chloride (800 mg) were added.

The reaction mixture was left at room temperature for 48 h, then the it was poured into ammonium chloride solution. The organic phase was was washed with brine (3×100 ml) and the solvent removed under vacuo to give the crude material which was purified by flash chromatography to give the title compound (1.72 g).IR (nujol) $cm^{-1}$: 1745, 1628, 1595. $^1$H-NMR (300 MHz, $D_2O$): 7.35 (t), 7.14 (t), 7.12 (d), 5.89 (bs), 4.30 (m), 4.00 (td), 3.97 (dd), 3.95 (d), 3.78 (m), 3.23 (s), 3.19 (d), 2.40 (s), 2.23 (m), 1.69 (m), 1.6–1.3 (m),1.35 (d), 0.91 (s), 0.12 (s). MS (FAB(+)NBA m/z: 490

Intermediate 16

3(3S,4R)-3-[(R)-1-t-butydimethylsilyloxy)ethyl]-4-((R)-2'-((S)-6'-[-N-[N'-methyl-N'-phenyl)aminocarbonyl]-N-methylamino-1'-oxocyclohexyl]-azetidin-2-one To a solution of oxalyl chloride (1.23 ml) in dry dichloromethane (150 ml) at −78° C. dimethyl sulfoxide (2.0 ml) in dry dichloromethane (40 ml) was added; after 15 min., a solution of intermediate 15 (1.7 g) in dry dichloromethane (40 ml) was added and the resulting mixture was left under stirring at −78° C. After 15 min. triethylamine (5.34 ml) was added and the reaction mixture warm up to 0° C., poured into a saturated ammonium chloride solution and extracted with ethyl acetate. The organic phase was was washed with brine (3×100 ml) and the solvent removed under vacuo to give the the title compound (1.67 g). IR ($CDCl_3$) $cm^{-1}$: 1757, 1718, 1653.

Intermediate 17

Allyl-(4S,8S,9R,10S,12R)-4-[N-[(N'-methyl-N'-phenyl)aminocarbonyl]-methylamino]-10-(1'dimethyl-t-butylsilyloxy)ethyl-11-oxo-1-azatricyclo[7.2.0.0$^{3,8}$]-undec-2-carboxylate To a solution of intermediate 16 (0.980 g) in dry dichloromethane (15 ml) at 0° C., solid potassium carbonate, allyloxalyl chloride (0.47 ml) and pyridine(0.28 ml) were added and the resulting mixture was left under stirring at 20° C. A further amount of allyloxalyl chloride (0.47 ml) and pyridine (0.28 ml) were added until complete reaction, then potassium carbonate was filtered off and the reaction mixture was washed with a 1% hydrogen chloride cold solution, the saturated sodium hydrogen carbonate and brine. The solvent was removed under vacuo to give the the crude compound which was purified by flash chromatography on silica gel, to give the title compound (0.90 g). Intermediate 4 (0.90 g) was dissolved in xylene (30 ml) and triethyl phosphite (1.3 ml) was added and the resulting mixture was left under stirring at 140° C. for 14 h. The reaction mixture was concentrated under vacuo to give the crude compound which was purified by flash chromatography on silica gel, to give the title compound (0.21 g).

IR ($CDCl_3$) $cm^{-1}$: 1767, 1728, 1641, 1597.

Intermediate 18

5-Allyl-(4S,8S,9R,10S,12R)-4-[N-[(N'-methyl-N'-phenyl)aminocarbonyl]-methylamino]-10-(1'hydroxyethyl-11-oxo-1-azatricyclo[7.2.0.0$^{3,8}$]-undec-2-carboxylate To a solution of intermediate 17 (0.210 g) in dry THF (19 ml) at 20° C., acetic acid (0.116 ml) and tetrabutylammonium fluoride (1M solution in THF) (1.5 ml) were added and the resulting mixture was left under stirring at 20° C. for 60 h. The reaction mixture was washed with a saturated sodium hydrogen carbonate solution (3×50 ml), ammonium chloride solution (3×50 ml) and brine (3×50 ml). The solvent was removed under vacuo to give the the crude compound which was purified by flash chromatography on silica gel, to give the title compound (0.10 g).

IR ($CDCl_3$) $cm^{-1}$: 1769, 1720, 1643.

Intermediate 19

(4S,8S,9R,10S,12R)-4-amino-10-(1'-hydroxyethyl)-11-oxo-1-azatricyclo[7.2.0.0$^{3,8}$]-undec-2-ene-2-carboxylic acid

Intermediate 20

(4S,8S,9R,10S,12R)-4-N-methylamino-10-(1'-hydroxyethyl)-11-oxo-1-azatricyclo[7,2,0,0$^{3,8}$]-undec-2-ene-2-carboxylic acid

EXAMPLE 1

Sodium-(4S,8S,9R,10S,12R)-4-(phenylaminocarbonylamino)-10-1'-hydroxyethyl-11-oxo-1-azatricyclo[7.2.0.0$^{3,8}$]-undec-2-ene-2-carboxylate (4S,8S,9R,10S,12R)-4-amino)-10-(1'-hydroxyethyl)-11-oxo-1-azatricyclo[7.2.0.0$^{3,8}$]-undec-2-ene-2-carboxylic acid (110 mg) was dissolved at 0°. in a mixture of tetrahydrofuran (3.5 ml) and 0.025M, pH=7 sodium phosphate buffer solution (6.5 ml). Phenyl isocyanate (2 ml) was added and the mixture stirred for 15 min. The solid diphenylurea was filtered. The aqueous solution was washed three times with ethyl acetate (10 ml), evaporated to reduce its volume (2 ml) then passed through a reverse phase column (techoprep 40–63 C18). The title compound (70 mg) was obtained by freeze drying the fraction eluted with a 10% solution of acetonitrile in water.

IR (nujol) Vmax cm—1: 1653 (C=O), 1749 (C=O B-lactam);

$^1$H-NMR (300 MHz, D2O): 7.22(t), 7.15(m), 7.01(t),5.17 (m), 4.07(m), 4.01(dd), 3.23(dd), 3.03(m),1.85(m), 1.78(m),1.7–1.5(m), 1.3–1.16(m) and 1.12(d) ppm. MS (VGquattro-FAB(+)NBA) m/z: 408

EXAMPLE 2

Sodium-(4S,8S,9R,10S,12R)-4-[4"-methoxyphenylaminocarbonyl)amino]-10-(1'- hydroxyethyl-11-oxo-1-azatricyclo[7.2.0.0³·⁸]-undec-2-ene-2-carboxylate

To a solution of (4S,8S,9R,10,12R) 4 amino-10-(1'-hydroxyethyl)-11-oxo-1-azatricyclo[7.2.0.0³·⁸]undec-2-ene-2-carboxylic acid (70 mg) in dry tetrahydrofuran (6 ml), trietheylamine (0.15 ml) was added under nitrogen at 22°. The solution was stirred for 10 min, then p-methoxyphenyl isocyanate (0.1 ml) was added. The obtained mixture was stirred for 15 min then filtered over celite. A 0.5M solution of sodium-2-ethylhexanoate in tetrahydrofuran (0.6 ml) was added to the filtrate. After 10 min the tetrahydrofuran solution was partially concentrated and treated with diethylether to give a solid which was centrifuged washed with ethyl acetate/diethylether 8/2 and dried to afford a white solid (65 mg). The solid was dissolved in water, washed three times with ethyl acetate (10 ml), then passed through a reverse phase column (techoprep 40–63 C18). The title compound (20 mg) was obtained by freeze drying the fraction eluted with a 10% solution of acetonitrile in water.

IR (nujul) Vmax cm–1: 1664 (C=O), 1750 (C=O B-lactam);

$^1$H-NMR (300 MHz, D$_2$O): 7.05 (m), 6.82(m), 5.14(m), 4.07(m), 3.98(dd), 3.67(s), 3.24(dd),3.03(m), 1.84(m), 1.76 (m), 1.68–1.50(m), 1.22(m) and 1.12(d) p.p.m.

MS (VGquattro-FAB(+)NBA) m/z: 438

EXAMPLE 3

Sodium-(4S,8S,9R,10S,12R)-4-[(4"-fluorophenylaminocarbonyl)amino]-10-(1'-hydroxyethyl)-11-oxo-1-azatricyclo[7.2.0.0³·⁸]-undec-2-ene-2-carboxylate To a solution of (4S,8S,9R,10S,12R) 4 amino-10-(1'-hydroxyethyl)-11-oxo-1-azatricyclo[7.2.0.0³·⁸]undec-2-ene-2-carboxylic acid (75 mg) in dry tetrahydrofuran (6 ml), triethylamine (0.17 ml) was added under nitrogen at 22° The solution was stirred for 10 min, then p-fluorophenyl isocyanate (0.1 ml) was added. The obtained mixture was stirred for 15 min then a 0.5M solution of sodium-2-ethylhexanoate in tetrahydrofuran (0.6 ml) was added. The tetrahydrofuran solution was partially concentrated and treated with diethylether to give a solid which was centrifuged washed with ethyl acetate/diethylether 8/2 and dried to afford title compound (47 mg) as a white solid.

IR (nujul) Vmax cm–1: 1672 (C=O), 1750 (C=O B-lactam);

$^1$H-NMR (300 MHz, D$_2$O): 7.10 (m), 6.94(m), 5.14(m), 4.07(m), 3.98(dd), 3.24(dd),3.03(m), 1.90–1.70(m), 1.68–1.46(m), 1.30–1.14(m) and 1.12(d) p.p.m.

MS (VGquattro-FAB(+)NBA) m/z: 426.

EXAMPLE 4

Sodium-(4S,8S,9R,10S,12R)-4-(benzylmethylaminocarbonylmethylamino)-10-(1'-hydroxyethyl)-11-oxo-1-azatricyclo[7.2.0.0³·⁸]undec-2-ene-2-carboxylate Intermediate 5 (0.220 g) was dissolved in a mixture of isopropanol (10 ml) and water (10 ml); then 5% palladium on activated carbon (0.022 g) and sodium hydrogen carbonate (0.035 g) were added. The mixture was hydrogenated (1 atm.) for 3 hrs, filtered on a celite pad and extracted with diethyl ether. The aqueous layer was freeze dried to give the title compound (0.175 g) as a white solid.

IR (CDCl$_3$) V$_{max}$ cm$^{-1}$: 1749, 1653.

$^1$H-NMR (300 MHz, D$_2$O): 7.27 (t), 7.19 (t), 7.13 (d), 4.76 (m), 4.34 (m), 4.06 (m), 3.93 (dd), 3.19 (dd), 2.80 (m), 2.73 (s), 2.59 (s), 2.11 (dm), 1.65 (m), 1.50–1.20 (m), 1.09 (d).

EXAMPLE 5

Sodium-(4S,8S,9R,10S,12R)-4-[N-[N-(2-pyridyl)-N-methylaminocarbonyl]-N-methyl]amino-10-(1'-hydroxyethyl)-11-oxo-1-azatricyclo[7.2.0.0³·⁸]undec-2-ene-2-carboxylate Intermediate 7 (0.110 g) was dissolved in a mixture of isopropanol (10 ml) and water (10 ml); then 5% palladium on activated carbon (0.011 g) and sodium hydrogen carbonate (0.018 g) were added. The mixture was hydrogenated (1 atm.) for 3 hrs, filtered on a celite pad and extracted with diethyl ether. The aqueous layer was freeze dried to give the title compound (0.070 g) as a white solid.

IR (CDCl$_3$)V$_{max}$ cm$^{-1}$: 1751, 1653, 1591.

$^1$H-NMR (300 MHz, D$_2$O): 8.1 (dd), 7.63 (td), 6.96 (t), 6.86 (d), 4.98 (bm), 4.04 (m), 3.89 (dd), 3.20 (dd), 3.06 (m), 2.88 (m), 2.66 (s), 2.08 (m), 1.72 (m), 1.60–1.20 (m), 1.08 (d).

EXAMPLE 6

Sodium-(4S,8S,9R,10S,12R)-4-[2-(2-pyridylethyl)methylaminocarbonylmethylamino]-10-(1'-hydroxyethyl)-11-oxo-1-azatricyclo[7.2.0.0³·⁸]undec-2-ene-2-carboxylate Intermediate 9(0.120 g) was dissolved in a mixture of isopropanol (10 ml) and water (10 ml); then 5% palladium on activated carbon (0.012 g) and sodium hydrogen carbonate (0.019 g) were added. The mixture was hydrogenated (1 atm.) for 3 hrs, filtered on a celite pad and extracted with diethyl ether. The aqueous layer was freeze dried to give the title compound (0.080 g) as a white solid.

$^1$H-NMR (300 MHz, D$_2$O): 8.27 n(d), 7.62 (m), 7.20 (d), 7.13 (m), 4.7 (m), 4.03 (m), 3.79 (dd), 3.52 (m), 3.14 (dd), 2.88 (m), 2.74 (s), 2.29 (s), 2.40 (m), 1.90 (m), 1.60 (m), 1.40–1.10 (m), 1.10 (d).

MS (VGquattro-FAB-NBA) m/z: 465.

EXAMPLE 7

Disodium (4S,8S,9R,10S,12R) 4-{N-[(1"-S-1-carboxyethyl)carbamoyl]-(N-methyl)}amino-10-[1'-hydroxyethyl]-11-oxo-1-azatricyclo[7.2.0.0³·⁸]undec-2-ene-2-carboxylate A suspension of intermediate 6 (130 mg), sodium hydrogen carbonate (30 mg), 10% palladium on carbon (13 mg) in isopropanol (15 ml) and water (15 ml) was hydrogenated at 1 atm for 1 h. After filtration, the solution was concentrated in vacuo to half volume and freeze dried. The residue was purified by preparative HPLC (technoprep 40–63 C18; elution acetonitrile/water 10:90) to give the title compound (8 mg) as a white solid.

IR (nujol) V$_{max}$ cm$^{-1}$: 3389 (OH and NH); 1770 and 1610 (C=O)

$^1$H-NMR (500 MHz, D$_2$O): 5.26 (dd); 4.15 (m); 4.06 (dd); 3.97 (q); 3.27 (dd); 3.07 (m); 2.94 (s); 2.10 (m); 1.86 (m); 1.76–1.54 (m); 1.27 (m); 1.23 (d); 1.20 (d).

MS (VGquattro-FAB-NBA) m/z:440

EXAMPLE 8

Sodium-[(4S,8S,9R,10S,12R)-4-[[(phenyl-N'-methyl)-amino]carbonyl-N-methylamino]-10-(1'hydroxyethyl-11-oxo-1-azatricyclo[7.2.0.03,8]-undec-2-carboxylate To a solution of intermediate 18 (0.10 g) in dry THF (4 ml) at 20° C. tetrakis(triphenylphosphine)palladium(O) (10 mg) and triethylphosphine (3 mg) were added at 20° C. After 10 min. sodium ethyl exanoate (0.5M solution in THF) (0.41 ml) was added and the resulting mixture was left under stirring for 30 min. A 1/1 diethyl ether/petroleum (10 ml) solution was then added, the solid was filtered, washed twice with the same mixture to give the title compound (42 mg).

$^1$H-NMR (300 MHz, D$_2$O): 7.27(m), 7.08 (m), 7.04 (m), 4.98 (m), 4.05 (m), 3.94(dd), 3.21 (dd), 3.04 (s), 2.83 (m), 2.45 (s), 2.03 (m), 1.70 (m), 1.56–1.24 (m), 1.14 (m), 1.09 9d).

EXAMPLE 9

Sodium-(4S,8S,9R,10S,12R)-4-(3"-pyridineaminocarbonylamino)-10-(1'-hydroxyethyl)-11-oxo-1-azatricyclo[7.2.0.0$^{3,8}$]-undec-2-ene-2-carboxylate (4S,8S,9R,10S,12R)-4-amino-10-(1'-hydroxyethyl)-11-oxo-1-azatricyclo[7.2.0.0$^{3,8}$]-undec-2-ene-2-carboxylic acid (130 mg) was suspended in acetonitrile(15 ml) at room temperature under a nitrogen atmosphere. Triethylamine(75 mg) was added to the reaction mixture which was then stirred at room temperature for 10 mins. Then 3-pyridine-isocyanate(0.4 g) was added and the mixture stirred for a further 20 mins. Next a 0.5M solution of sodium-2-ethylhexanoate(1.0 ml) was added to the stirred reaction mixture. Stirring was continued for a further 10 mins., after which the volume of solvent was reduced by half in vacuo. Acetone(10 ml) and light petroleum(10 ml) were then added to the reaction mixture. This resulted in the precipitation of an off-white solid, which was filtered, washed with ethyl acetate(2×30 ml), diethyl ether(2×30 ml),and dried to afford the title compound (107 mg) as a white solid.

IR(nujol) Vmax cm$^{-1}$: 3340–3194(N—H), 1755(C=O, b-lactam), 1680(C=C, C=N).

$^1$H-NMR (300 MHz, D$_2$O):8.30(bs), 8.05(d), 7.63(d), 7.22(dd), 5.16(bs), 4.04(m), 3.85(dd), 3.22(m), 3.01(m), 1.83(m), 1.8–1.7(m), 1.65–1.50(m), 1.3–1.2(m), and 1.09 (d).

EXAMPLE 10

Sodium-(4S,8S,9R,10S,12R)-4-[(2"-hydroxyphenylaminocarbonyl)amino]-10-(1'-hydroxyethyl)-11-oxo-1-azatricyclo[7,2,0,0$^{3,8}$]-undec-2-ene-2-carboxylate To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (200 mg) in acetone (30 ml), triethylamine (0.15 ml) was added under nitrogen at 22°. The solution was stirred for 10 min, then o-allyloxycarbonyloxyphenyl isocyanate (245 mg) was added. The obtained solution was stirred for 15 min, then a solution of dimedone (159 mg) and tetrakis (triphenylphosphine)-palladium (0) (26 mg) in acetone (3 ml) was added. The resulting solution was stirred for 90 min, then a 0.5M solution of sodium-2-ethylexanoate in tetrahydrofuran (1.5 ml) was added. After 10 min the mixture was partially concentrated and stirred for 1 h, the solid was centrifuged, washed with ethyl acetate and ether and dried to afford a white solid (180 mg). The solid was purified by preparative HPLC (column techoprep 40–63 C18). The title compound (36 mg) was obtained by freeze drying the fraction elueted with a 10% of acetonitrile in water.

IR (nujul) Vmax cm–1: 1599 (C=O), 1761 (C=O β-lactam), 3341 (O—H, N—H);

1H-NMR (300 MHz, D2O): 7.19(m), 6.96(m), 6.79(m), 5.18(m), 4.07(m), 3.99(dd), 3.23(dd), 3.04(m), 2.10(m), 1.12(d) p.p.m.

EXAMPLE 11

Sodium-(4S,8S,9R,10S,12R)-4-[(4"-methylsuphonylphenylaminocarbonyl)amino]-10-1'-hydroxyethyl)-11-oxo-1-azatricyclo[7,2,0,0$^{3,8}$]-undec-2-ene-2-carboxylate.

To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.08 ml) was added under nitrogen at 22° C. The solution was stirred for 10 min, then p-methylsulphonylphenyl isocyanate (111 mg) was added. The obtained solution was stirred for 15 min, then a 0.5M solution of sodium-2-ethylexanoate in tetrahydrofuran (0.75 ml) was added. After 10 min the mixture was partially concentrated and treated with petroleum ether to give a solid which was centrifuged, washed with petroleum ether/ acetone 2/1 and dried to afford title compound (109 mg) as a pale yellow solid.

IR (nujol) Vmax cm–1: 1693 (C=O), 1755 (C=O β-lactam), 3331 (O—H, N—H);

1H-NMR (300 MHz, D$_2$O): 7.69(d), 7.43(d), 5.19(m), 4.05(m), 3.95(dd), 3.22(dd), 3.07(s), 3.03(m), 1.88–1.70(m), 1.30–1.00(m), 1.09(d) p.p.m.

EXAMPLE 12

Sodium (4S,8S,9R,10S,12R)-4-(uracil-5'-amino) carbonylamino-10-(1'-hydroxyethyl)-11-oxo-1-aza-tricyclo [7.2.0.0$^{3,8}$]-undec-2-ene carboxylate To a suspension of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetonitrile (15 ml), triethylamine (0.10 ml) was added under nitrogen at 22° C. The suspension was stirred for 5 min and then uracyl-5-isocyanate (75 mg) was added and reaction stirred at 70° C. for 1 hour, then more isocyanate (20 mg) was added and reaction stirred at 70° C. for further 40'. The resulting suspension was cooled, solvent evaporated and residue resuspended in acetone (15 ml). Sodium 2-ethylhexanoate (0.75 ml of a 0.5M solution in THF) was added, suspension stirred for for 30' under N$_2$ and then filtered, washing with ethyl acetate and diethyl ether, to give 400 mg of a solid which was purified by preparative HPLC (column techoprep 40–63 C18) to afford the title compound as a white solid (31 mg)

IR (nujol) Vmax cm–1: 1666 (C=O), 1713 (C=Oβ-lactam), 3335–3202 (O—H, N—H); 1H-NMR (300 MHz, D$_2$O, ppm): 7.47(bs), 5.10(bs), 4.06(m), 3.99(dd), 3.22(dd), 3.00(s), 1.80–1.70(m), 1.30–1.10(m), 1.10(d)

EXAMPLE 13

Sodium-(4S,8S,9R,10S,12R)-4-(3"-picolylaminocarbonylamino)-10-(1'-hydroxyethyl)-11-oxo-1-azatricyclo[7.2.0.0$^{3,8}$]-undec-2-ene-2-carboxylate (4S,8S,9R,10S,12R)-4-amino-10-(1'-hydroxyethyl)-11-oxo-1-azatricyclo[7.2.0.0$^{3,8}$]-undec-2-ene-2-carboxylic acid (120 mg) was suspended in acetone(20 ml) at room temperature under a nitrogen atmosphere. Triethylamine(0.2 ml) was added to the reaction mixture which was then stirred at room temperature for 10 mins. Then 3-picolyl-aminocarbonylimidazole (0.45 g) was added and the mixture stirred at 50° C. for 1 hr. The solution was cooled at 0° C. and a 0.5M solution of sodium-2-ethylhexanoate(0.8 ml) was added to the stirred reaction mixture. Stirring was continued for a further 10 mins., after which the volume of solvent was reduced by half in vacuo. This resulted in the precipitation of an off-white solid, which was filtered, washed with ethyl acetate(2×30 ml), diethyl ether(2×30 ml),and dried to afford the title compound (120 mg) as a white solid.

IR(nujol) Vmax cm$^{-1}$: 3265(N—H), 1751 (C═O, β-lactam).

$^1$H-NMR (300 MHz, D$_2$O):8.2(m), 7.51(d), 7.25(m), 4.96 (bm), 4.34(d), 4.1–4.0(m),3.84(dd), 3.16(dd), 2.90(m), 1.8–1.7(m), 1.6–1.4(m), 1.25(m), and 1.09(d).

EXAMPLE 14

Sodium-(4S,8S,9R,10S,12R)-4-(2"-furfurylaminocarbonylamino)-10-(1'-hydroxyethyl)-11-oxo-1-azatricyclo[7.2.0.0$^{3,8}$]-undec-2-ene-2-carboxylate (4S,8S,9R,10S,12R)-4-amino-10-(1'-hydroxyethyl)-11-oxo-1-azatricyclo[7.2.0.0$^{2,8}$]-undec-2-ene-2-carboxylic acid (130 mg) was suspended in acetone(20 ml) at room temperature under a nitrogen atmosphere. Triethylamine(0.2 ml) was added to the reaction mixture which was then stirred at room temperature for 10 mins. Then 2-furfurylaminocarbonylimidazole (0.45 g) was added and the mixture stirred at 50° C. for 1 hr. The solution was cooled at 0° C. and a 0.5M solution of sodium-2-ethylhexanoate(0.8 ml) was added to the stirred reaction mixture. Stirring was continued for a further 10 mins., after which the volume of solvent was reduced by half in vacuo. This resulted in the precipitation of an off-white solid, which was filtered, washed with ethyl acetate(2×30 ml), diethyl ether(2×30 ml),and dried to afford the title compound (60 mg) as a white solid.

IR(nujol) Vmax cm$^{-1}$: 3302(N—H), 1753(C═O, β-lactam).

$^1$H-NMR (300 MHz, D$_2$O):7.25(m), 6.21 (dd), 6.02(d), 4.95(m), 4.22(d), 4.04(m), 3.98(d),3.85(dd), 3.16(dd), 2.89 (m), 1.8–1.64(m), 1.6–1.38(m), 1.3–1.0(m), 1.09(d).

EXAMPLE 15

Sodium-(4S,8S,9R,10S,12R)-4-[(2"-methoxyphenylaminocarbonyl)amino]-10-(1'-hydroxyethyl)-11-oxo-1azatricyclo[7,2,0,0$^{3,8}$]-undec-2-ene-2-carboxylate To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.100 ml) was added under nitrogen at 22° C. followed by o-methoxyphenyl isocyanate (0.078 ml). The solution obtained was stirred for 60 min then a 0.5M solution of sodium-2-ethylhexanoate in tetrahydrofuran (0.67 ml) was added. After 10 min the mixture was partially concentrated and treated with petroleum ether (8 ml) to give a precipitate which was filtered under N$_2$, washed with petroleum ether/acetone 2/1 then petroleum ether, and dried to afford the title compound (102.6 mg) as a white solid.

IR (nujol) Vmax cm–1: 1753 (C═O β-lactam), 3339 (N—H);

1H-NMR (300 MHz, D$_2$O): 7.30(d, 1H), 7.00(t, 1H), 6.92(d, 1H), 6.34(t, 1H), 5.18(s,1H), 4.07(m,1H), 3.99(dd, 1H), 3.68(s,3H), 3.22(dd,1H), 3.02(s,1H), 1.90–1.70(m,2H), 1.70–1.50(m,2H), 1.30–1.10(m,2H), 1.12(d,3H) p.p.m.

EXAMPLE 16

Sodium-(4S,8S,9R,10S,12R)-4-[(benzylaminocarbonyl)amino]-10-(1'-hydroxyethyl)-11-oxo-1-azatricyclo[7,2,0,0$^{3,8}$]-undec-2-ene-2-carboxylate To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.100 ml) was added under nitrogen at 22° C. The solution was stirred for 10 min then benzyl isocyanate (0.070 ml) was added. The solution obtained was stirred for 40 min then a 0.5M solution of sodium-2-ethylhexanoate in tetrahydrofuran (0.74 ml) was added. After 15 min the mixture was partially concentrated and treated with petroleum ether to give a precipitate which was filtered under N$_2$, washed with petroleum ether/acetone 2/1 then petroleum ether and dried to afford the title compound (67 mg) as a white solid.

IR (nujol) Vmax cm–1: 1757 (C═O β-lactam), 3320 (N—H);

1H-NMR (300 MHz, D$_2$O): 7.30–7.10(m,5H), 4.99(s, 1H), 4.28(d,1H), 4.10–4.00(m,2H), 3.85(dd,1H), 3.17(dd, 1H), 2.89(m,1H), 1.84–1.64(m,2H), 1.60–1.40(m,2H), 1.30–1.10(m,2H), 1.11(d,3H) p.p.m.

EXAMPLE 17

Sodium-(4S,8S,9R,10S,12R)-4-[(3"-cyanophenylaminocarbonyl)amino]-10-(1-hydroxyethyl)-11-oxo-1-azatricyclo[7,2,0,0$^{3,8}$]-undec-2-ene-2-carboxylate.

To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.100 ml) was added under nitrogen at 22° C. followed by m-cyanophenyl isocyanate (82 mg). The solution obtained was stirred for 90 min then a further portion of m-cyanophenyl isocyanate was added (27 mg). The mixture was stirred for 30 min and then filtered giving a solution to which was added a 0.5M solution of sodium-2-ethylhexanoate in tetrahydrofuran (0.67 ml). After 5 min the mixture was partially concentrated and treated with petroleum ether (7 ml) to give a precipitate which was filtered under N$_2$, washed with petroleum ether/acetone 2/1 then petroleum ether, and dried to afford the title compound (73.5 mg) as a white solid.

IR (nujol) Vmax cm–1: 1680(C═O), 1753 (C═O β-lactam), 2250(CN), 3300 (O—H, N—H);

1H-NMR (300 MHz, D$_2$O): 7.60(s, 1H), 7.41(m,1H), 7.32(m,2H), 5.18(m,1H), 4.07(m,1H), 3.97(dd,1H), 3.24 (dd,1H), 3.02(m,1H), 1.85(m,1H), 1.76(m,1H), 1.70–1.48 (m,3H), 1.30–1.10(m,1H), 1.12(d,3H) p.p.m.

EXAMPLE 18

Sodium-(4S,8S,9R,10S,12R)-4-[(2"-phenoxyethylaminocarbonyl)amino]-10-(1'-hydroxyethyl)-11-oxo-1-azatricyclo[7,2,0,0$^{3,8}$]-undec-2-ene-2-carboxylate.

To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.100 ml) was added under nitrogen at 22° C. then phenoxyethyl isocyanate (0.200 ml) was added. The solution obtained was stirred for 2.5 h then a 0.5M solution of sodium-2-ethylhexanoate in tetrahydrofuran (0.700 ml) was added. After 10 min the mixture was filtered under N$_2$, washed with ethyl acetate (2×50 ml) and diethyl ether (2×50 ml), then dried to afford the title compound (119.3 mg) as a white solid.

IR (nujol) Vmax cm–1: 1653(C═O), 1751 (C═Oβ-lactam), 3310 (N—H);

1H-NMR (400 MHz, D$_2$O): 7.19(td,2H), 6.87(t, 1H), 6.81(dd,2H), 4.90(bm, 1H), 3.92(m,1H), 3.88(m,2H), 3.83 (m,1H), 3.50(ddd, 1H), 3.17(ddd,1H), 3.04(dd,1H), 2.77(m, 1H), 1.74(m,1H), 1.63(m,1H), 1.48(m,3H), 1.13(m,1H), 1.05(d,3H), p.p.m.

EXAMPLE 19

Sodium-(4S,8S,9R,10S,12R)-4-[(4"-acetamidophenylaminocarbonyl)amino]-10-(1'-hydroxyethyl)-11-oxo-1-azatricyclo[7,2,0,0$^{3,8}$]-undec-2-ene-2-carboxylate.

To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.100 ml) was added under nitrogen at 22° C. followed by p-acetamidophenyl isocyanate (100 mg). The solution obtained was stirred for 30 min then H$_2$O mQ (3 ml) was added. After 60 min a 0.5M solution of sodium-2-ethylhexanoate in tetrahydrofuran (0.670 ml) was added stirring was continued for 10 min then the mixture was partially concentrated and azeotroped several times with acetonitrile. The resulting solid was suspended in acetone, filtered and washed with ethyl acetate (2×50 ml), diethyl ether (2×50 ml) and dried to afford the title compound (123.5 mg) as a white solid.

IR (nujol) Vmax cm–1: 1661 (C=O), 1755 (C=O β-lactam), 3304 (O—H,N—H);

1H-NMR (400 MHz, D$_2$O): 7.19(d,2H). 7.13(d,2H), 5.15 (m,1H), 4.06(m,1H), 3.96(dd,1H), 3.23(dd,1H), 3.02(m, 1H), 1.99(s,3H), 1.90–1.70(m,2H), 1.70–1.45(m,3H), 1.32–1.00(m, 1H), 1.11(d,3H) p.p.m.

EXAMPLE 20

Sodium-(4S,8S,9R,10S,12R)-4-[(4"-cyanophenylaminocarbonyl)amino]-10-(1'-hydroxyethyl)-11-oxo-1-azatricyclo[7,2,0,0$^{3,8}$]-undec-2-ene-2-carboxylate.

To a solution of (4S,8S,9R,10S,12R)-4-amino-10-(1'-hydroxyethyl)-11-oxo-1-azatricyclo[7,2,0,0$^{3,8}$]-undec-2-ene-2-carboxylic acid (100 mg) in acetone (15 ml), triethylamine (0.100 ml) was added under nitrogen at 22° C. followed by p-cyanophenyl isocyanate (0.081 mg). The solution obtained was stirred for 60 min then a 0.5M solution of sodium-2-ethylhexanoate in tetrahydrofuran (0.74 ml) was added. After 10 min the mixture was partially concentrated and treated with petroleum ether (8 ml) to give a precipitate which was filtered under N$_2$, washed with petroleum ether/acetone 2/1 then petroleum ether, and dried to afford the title compound (102.6 mg) as a white solid.

IR (nujol) Vmax cm–1: 1695(C=O), 1749 (C=O β-lactam), 2280(CN), 3352 (O—H,N—H);

1H-NMR (300 MHz, D$_2$O): 7.52(m,2H), 7.31(m,2H), 5.18(m,1H), 4.05(m,1H), 3.94(dd, 1H), 3.22(dd,1H), 3.00 (m,1H), 1.86–1.70(m,2H), 1.70–1.46(m,3H), 1.30–1.00(m, 1H), 1.09(d,3H) p.p.m.

EXAMPLE 21

Sodium-(4S,8S,9R, 10S, 12R)-4-(aminocarbonyl-N-methylamino)-10-(1'hydroxyethyl)-11-oxo-1-azatricyclo[7.2.0.0$^{3,8}$]-undec-2ene-2-carboxylate To a solution of (4S,8S,9R,10S,12R)-4-N-methylamino-10-(1'hydroxyethyl)-11-oxo-1-azatricyclo[7.2.0.0$^{3,8}$]-undec-2-carboxylic acid (116 mg) in a mixture of water (5.5 ml) and acetone (3 ml) at 20° C. a solution of sodium hydrogen carbonate (36 mg) in water (0.5 ml) was added; after 10 min. trimethylsilyl isocyanate (0.28 ml) was added.

Further amounts of trimethylsilyl isocyanate were required (4×0.28 ml) to obtain complete reaction. The reaction mixture was concentrated under vacuo and the crude compound passed through a reverse phase column (techoprep 40–63 C18).

The title compound (30 mg) was obtained by freeze drying the fraction eluted with a 10% solution of acetonitrile in water.

$^1$H-NMR (300 MHz, D$_2$O): 5.14(bm), 4.06 (m), 3.97(dd), 3.20 (dd), 3.00 (m), 2.85 (s), 1.98 (m), 1.80 (m), 1.70–1.60 (m), 1.10 (d). MS (VGquattro-FAB(+)NBA m/z: 346

The following examples No's 22–91 were prepared from Intermediates 19 or 20 by reaction with the appropriate isocyanate R$_2$NCO or amine R$_2$NH$_2$ Details of the reaction conditions used are also included in the table given below.

22
Sodium-(4S,8S,9R,10S,12R)-4-(4"-trifluoromethylphenylaminocarbonylamino)-10-(1'-hydroxyethyl)-11-oxo-1-azatricyclo[7.2.0.0$^{3,8}$]-undec-2-ene-2-carboxylate

23
Sodium-(4S,8S,9R,10S,12R)-4-[(4"-methylphenylaminocarbonyl)amino]-10-(1'-hydroxyethyl)-11-oxo-1-azatricyclo[7,2,0,0$^{3,8}$]-undec-2-ene-2-carboxylate.

24
Sodium-(4S,8S,9R,10S,12R)-4-[(4"-nitrophenylaminocarbonyl)amino]-10-(1'-hydroxyethyl)-11-oxo-1-azatricyclo[7,2,0,0$^{3,8}$]-undec-2-ene-2-carboxylate.

25
Sodium-(4S,8S,9R,10S,12R)-4-(4"-chlorophenylaminocarbonylamino)-10-(1'-hydroxyethyl)-11-oxo-1-azatricyclo[7.2.0.0$^{3,8}$]-undec-2-ene-2-carboxylate

26
Sodium-(4S,8S,9R,10S,12R)-4-[(3"-nitrophenylaminocarbonyl)amino]-10-(1'-hydroxyethyl)-11-oxo-1-azatricyclo[7,2,0,0$^{3,8}$]-undec-2-ene-2-carboxylate.

27
Sodium-(4S,8S,9R,10S,12R)-4-[(4"-dimethylaminosulfonylphenylaminocarbonyl)amino]-10-(1'-hydroxyethyl)-11-oxo-1-azatricyclo[7,2,0,0$^{3,8}$]-undec-2-ene-2-carboxylate.

28
Sodium-(4S,8S,9R,10S,12R)-4-(2"-dimethylaminocarbonylphenylaminocarbonylamino)-10-(1'-hydroxyethyl)-11-oxo-1-azatricyclo[7.2.0.0$^{3,8}$]-undec-2-ene-2-carboxylate

29
Sodium-(4S,8S,9R,10S,12R)-4-[(2"-chlorophenylaminocarbonyl)amino]-10-(1'-hydroxyethyl)-11-oxo-1-azatricyclo[7,2,0,0$^{3,8}$]-undec-2-ene-2-carboxylate.

30
Sodium-(4S,8S,9R,10S,12R)-4-[(3"-trifluoromethylphenylaminocarbonyl)amino]-10-(1'-hydroxyethyl)-11-oxo-1-azatricyclo[7,2,0,0$^{3,8}$]-undec-2-ene-2-carboxylate.

31
Sodium-(4S,8S,9R,10S,12R)-4-[(2"-trifluoromethylphenylaminocarbonyl)amino]-10-(1'-hydroxyethyl)-11-oxo-1-azatricyclo[7.2.0.0$^{3,8}$]-undec-2-ene-2-carboxylate

32
Sodium-(4S,8S,9R,10S,12R)-4-[(4"-trifluoromethylpyrid-3"-yl-aminocarbonyl)amino]-10-(1'-hydroxyethyl)-11-oxo-1-azatricyclo[7,2,0,0$^{3,8}$]-undec-2-ene-2-carboxylate.

33
Sodium-(4S,8S,9R,10S,12R)-4-[(3"-dimethylaminosulfonylphenylaminocarbonyl)amino]-10-1'-

33 hydroxyethyl)-11-oxo-1-azatricyclo[7,2,0,0³·⁸]-undec-2-ene-2-carboxylate.

34

Sodium (4S,8S,9R,10S,12R)-4-(1",3"-dimethyluracil-5"-amino)carbonylamino-10-(1-hydroxyethyl)-11-oxo1-azatricyclo[7.2.0.0³·⁸]-undec-2-ene carboxylate

35

Sodium-(4S,8S,9R,10S,12R)-4-(2"-methylsulfonyloxyphenylaminocarbonylamino)-10-(1'-hydroxyethyl)-11-oxo-1-azatricyclo[7.2.0.0³·⁸]-undec-2-ene-2-carboxylate

36

Sodium-(4S,8S,9R,10S,12R)-4-(5"-N-methyl-2"-pyridon-aminocarbonylamino)-10-(1'-hydroxyethyl)-11-oxo-1-azatricyclo[7.2.0.0³·⁸]-undec-2-ene-2-carboxylate

37

Sodium-(4S,8S,9R,10S,12R)-4-[(cyclohexylaminocarbonyl)amino]-10-(1'-hydroxyethyl)-11-oxo-1-azatricyclo[7,2,0,0³·⁸]-undec-2-ene-2-carboxylate.

38

Sodium-(4S,8S,9R,10S,12R)-4-[(3"-furylaminocarbonyl)amino]-10-(1'-hydroxyethyl)-11-oxo-1-azatricyclo[7,2,0,0³·⁸]-undec-2-ene-2-carboxylate.

39

Sodium-(4S,8S,9R,10S,12R)-4-[(cyclopropylaminocarbonyl)amino]-10-(1'-hydroxyethyl)-11-oxo-1-azatricyclo[7,2,0,0³·⁸]-undec-2-ene-2-carboxylate.

40

Sodium-(4S,8S,9R,10S,12R)-4-[[3-(N-methylpyridinium)methylaminocarbonylamino]-10-(1'-hydroxyethyl)-11-oxo-1-azatricyclo[7,2,0,0³·⁸]-undec-2-ene-2-carboxylate.

41

Sodium-(4S,8S,9R,10S,12R)-4-[(1"methyl-1H-pyrrol-2"-yl-aminocarbonyl)amino]-10-(1'-hydroxyethyl)-11-oxo-1-azatricyclo[7,2,0,0³·⁸]-undec-2-ene-2-carboxylate.

42

Sodium-(4S,8S,9R,10S,12R -4-4"-chlorobenzylaminocarbonyl)amino]-10-1'-hydroxyethyl)-11-oxo-1-azatricyclo[7,2,0,0³·⁸]-undec-2-ene-2-carboxylate

43

Sodium-(4S,8S,9R,10S,12R)-4-2"-phenylethylaminocarbonyl)amino]-10-1'-hydroxyethyl)-11-oxo-1-azatricyclo[7,2,0,0³·⁸]-undec-2-ene-2-carboxylate.

44

Sodium-(4S,8S,9R,10S,12R)-4-2"-furylaminocarbonyl)amino]-10-(1'-hydroxyethyl)-11-oxo-1-azatricyclo[7,2,0,0³·⁸]-undec-2-ene-2-carboxylate.

45

Sodium (4S,8S,9R,10S,12R)-4-(3"-thiophen-aminocarbonylamino)-10-(1-hydroxyethyl)-11-oxo1-azatricyclo[7.2.0.0³·⁸]-undec-2-ene carboxylate.

46

Sodium-4S,8S,9R,10S,12R)-4-2"-thiophen-aminocarbonylamino -10-1'-hydroxyethyl)-11-oxo-1-azatricyclo[7.2.0.0³·⁸]-undec-2-ene-2-carboxylate.

47

Sodium-4S,8S,9R,10S,12R)-4-2"-methyl-thiophen-5"-yl-aminocarbonylamino)-10-(1'-hydroxyethyl-11-oxo-1-azatricyclo[7.2.0.0³·⁸]-undec-2-ene-2-carboxylate.

48

Sodium-4S,8S,9R,10S,12R)-4-2"-phenyl-pyridin-5"-yl-aminocarbonyl)amino]-10-1'-hydroxyethyl-11-oxo-1-azatricyclo[7,2,0,0³·⁸]-undec-2-ene-2-carboxylate.

49

Sodium-(4S,8S,9R,10S,12R)-4-[(3"-bromopyridin-5"yl-aminocarbonyl)amino]-10-(1'-hydroxyethyl)-11-oxo-1-azatricyclo[7,2,0,0³·⁸]-undec-2-ene-2-carboxylate.

50

Sodium-(4S,8S,9R,10S,12R)-4-[(2",3"-dichloro-pyridin-5"yl-aminocarbonyl)amino]-10-(1'-hydroxyethyl)-11-oxo-1-azatricyclo[7,2,0,0³·⁸]-undec-2-ene-2-carboxylate.

51

Sodium-(4S,8S,9R,10S,12R)-4-[(2"-chloro-pyridin-5"yl-aminocarbonyl)amino]-10-(1'-hydroxyethyl)-11-oxo-1-azatricyclo[7,2,0,0³·⁸]-undec-2-ene-2-carboxylate.

52

Sodium-(4S,8S,9R,10S,12R)-4-[(4"-methyl-1",2",3"-thiadiazol-5"-yl-aminocarbonyl)amino]-10-(1'-hydroxyethyl)-11-azatricyclo[7,2,0,0³·⁸]-undec-2-ene-2-carboxylate.

53

Sodium-(4S,8S,9R,10S,12R)-4-[(1",2",3"-thiadiazol-4"-yl-aminocarbonyl)amino]-10-(1'-hydroxyethyl)-11-oxo-1-azatricyclo[7,2,0,0³·⁸]-undec-2-ene-2-carboxylate.

54

Sodium-(4S,8S,9R,10S,12R)-4-[(2"-phenylethylaminocarbonyl)methylamino]-10-(1'-hydroxyethyl)-11-oxo-1-azatricyclo[7.2.0.0³·⁸]-undec-2-ene-2-carboxylate

55

Sodium-(4S,8S,9R,10S,12R)-4-[(4"-chlorobenzylaminocarbonyl)methylamino]-10-(1'-hydroxyethyl)-11-oxo-1-azatricyclo[7,2,0,0³·⁸]-undec-2-ene-2-carboxylate.

56

Sodium-(4S,8S,9R,10S,12R)-4-[(phenoxyethylaminocarbonyl)methylamino]-10-(1'-hydroxyethyl)-11-oxo-1-azatricyclo[7,2,0,0³·⁸]-undec-2-ene-2-carboxylate.

57

Sodium-(4S,8S,9R,10S,12R)-4-[(3"-picolylaminocarbonyl)methylamino]-10-(1'-hydroxyethyl)-11-oxo-1-azatricyclo[7.2.0.0³·⁸]-undec-2-ene-2-carboxylate

58

Sodium-(4S,8S,9R,10S,12R)-4-[(ethoxycarbonylmethylaminocarbonyl)methylamino]-10-(1'-hydroxyethyl)-11-oxo-1-azatricyclo[7,2,0,0³·⁸]-undec-2-ene-2-carboxylate.

59

Sodium-(4S,8S,9R,10S,12R)-4-[(2"-hydroxyethylaminocarbonyl)methylamino]-10-(1'-hydroxyethyl)-11-oxo-1-azatricyclo[7,2,0,0³·⁸]-undec-2-ene-2-carboxylate.

60

Sodium-(4S,8S,9R,10S,12R)-4-(2"-chloroethylaminocarbonylamino)-10-(1'-hydroxyethyl)-11-oxo-1-azatricyclo[7.2.0.0³·⁸]-undec-2-ene-2-carboxylate

61

Sodium-(4S,8S,9R,10S,12R)-4-[(2"-hydroxyethylaminocarbonyl)amino]-10-(1'-hydroxyethyl)-11-oxo-1-azatricyclo[7,2,0,0³·⁸]-undec-2-ene-2-carboxylate.

62

Sodium-(4S,8S,9R,10S,12R)-4-[(5"-ethoxycarbonylpentylaminocarbonyl)methylamino]-10-(1'-hydroxyethyl)-11-oxo-1-azatricyclo[7,2,0,0³·⁸]-undec-2-ene-2-carboxylate.

63

Sodium-(4S,8S,9R,10S,12R)-4-[(2"-trimethylammoniumethylaminocarbonyl)amino]-10-(1'-hydroxyethyl)-11-oxo-1-azatricyclo[7.2.0.0³·⁸]-undec-2-ene-2-carboxylate

64

Sodium-(4S,8S,9R,10S,12R)-4-[(2"-azidoethylaminocarbonyl)amino]-10-(1'-hydroxyethyl)-11-oxo-1-azatricyclo[7,2,0,0³·⁸]-undec-2-ene-2-carboxylate.

65 Sodium-(4S,8S,9R,10S,12R)-4-[(4"-N-formylpiperidin-aminocarbonyl)methylamino]-10-(1'-hydroxyethyl)-11-oxo-1-azatricyclo[7,2,0,0$^{3,8}$]-undec-2-ene-2-carboxylate.

66 Sodium-(4S,8S,9R,10S,12R)-4-[(tetrahydropyran-4"-yl-aminocarbonyl)methylamino]-10-(1-hydroxyethyl)-11-oxo1-azatricyclo[7.2.0.0$^{3,8}$]-undec-2-ene carboxylate 67 Sodium-(4S,8S,9R,10S,12R)-4-[4"-((N-allyloxycarbonyl)piperidin-aminocarbonyl)methylamino]-10-(1'-hydroxyethyl)-11-oxo-1-azatricyclo[7.2.0.0$^{3.8}$]-undec-2-ene-2-carboxylate 68 Sodium-(4S,8S,9R,10S,12R)-4-[(cyclohexylaminocarbonyl)methylamino]-10-(1'-hydroxyethyl)-11-oxo-1-azatricyclo[7.2.0.0$^{3.8}$]-undec-2-ene-2-carboxylate 69 Sodium-(4S,8S,9R,10S,12R)-4-[(benzylaminocarbonyl)methylamino]-10-(1'-hydroxyethyl)-11-oxo-1-azatricyclo[7,2,0,0$^{3,8}$]-undec-2-ene-2-carboxylate.

70 Sodium-(4S,8S,9R,10S,12R)-4-[(ethylaminocarbonyl)methylamino]-10-(1'-hydroxyethyl)-11-oxo-1-azatricyclo[7,2,0,0$^{3,8}$]-undec-2-ene-2-carboxylate.

71 Sodium-(4S,8S,9R,10S,12R)-4-[(tert-butylaminocarbonyl)methylamino]-10-(1'-hydroxyethyl)-11-oxo-1-azatricyclo[7,2,0,0$^{3,8}$]-undec-2-ene-2-carboxylate.

72 Sodium-(4S,8S,9R,10S,12R)-4-[(cyclopropylaminocarbonyl)methylamino]-10-(1'-hydroxyethyl)-11-oxo-1-azatricyclo[7,2,0,0$^{3,8}$]-undec-2-ene-2-carboxylate.

73 Sodium-(4S,8S,9R,10S,12R)-4-[(4"-aminosulfonylbenzylaminocarbonyl)amino]-10-(1'-hydroxyethyl)-11-oxo-1-azatricyclo[7,2,0,0$^{3,8}$]-undec-2-ene-2-carboxylate.

74 Sodium-(4S,8S,9R,10S,12R)-4-[(2"-methoxycarbonylphenylaminocarbonyl)amino]-10-(1"-hydroxyethyl)-11-oxo-1-azatricyclo[7,2,0,0$^{3,8}$]-undec-2-ene-2-carboxylate.

75 Sodium-(4S,8S,9R,10S,12R)-4-[(2"-isopropylphenylaminocarbonyl)amino]-10-(1'-hydroxyethyl)-11-oxo-1-azatricyclo[7,2,0,0$^{3,8}$]-undec-2-ene-2-carboxylate.

76 Sodium-(4S,8S,9R,10S,12R)-4-(4"-bromophenylaminocarbonyamino)-10-(1'-hydroxyethyl)-11-oxo-1-azatricyclo[7,2,0,0$^{3,8}$]-undec-2-ene-2-carboxylate.

77 Sodium-(4S,8S,9R,10S,12R)-4-(3"-chloro-4"-fluorophenylaminocarbonylamino)-10-(1-hydroxyethyl)-11-oxo1-azatricyclo[7.2.0.0$^{3,8}$]-undec-2-ene carboxylate 78 Sodium-(4S,8S,9R,10S,12R)-4-(4"-methoxyphenylaminocarbonylamino)-10-(1'-hydroxyethyl)-11-oxo-1-azatricyclo[7.2.0.0$^{3.8}$]-undec-2-ene-2-carboxylate 79 Sodium-(4S,8S,9R,10S,12R)-4-(3",4",5"-trimethoxyphenylaminocarbonylamino)-10-(1'-hydroxyethyl)-11-oxo-1-azatricyclo[7.2.0.0$^{3,8}$]-undec-2-ene-2-carboxylate 80 Sodium-(4S,8S,9R,10S,12R)-4-[(2"-nitrophenylaminocarbonyl)amino]-10-(1'-hydroxyethyl)-11-oxo-1-azatricyclo[7,2,0,0$^{3,8}$]-undec-2-ene-2-carboxylate.

81 Sodium-(4S,8S,9R,10S,12R)-4-[(3"-methylthiophenylaminocarbonyl)amino]-10-(1'-hydroxyethyl)-11-oxo-1-azatricyclo[7,2,0,0$^{3,8}$]-undec-2-ene-2-carboxylate.

82 Sodium-(4S,8S,9R,10S,12R)-4-[(2"-methylsulfonylphenylaminocarbonyl)amino]-10-(1'-hydroxyethyl)-11-oxo-1-azatricyclo[7,2,0,0$^{3,8}$]-undec-2-ene-2-carboxylate.

83 Sodium-(4S,8S,9R,10S,12R)-4-[(2"-methylsulfinylphenylaminocarbonyl)amino]-10-(1'-hydroxyethyl)-11-oxo-1-azatricyclo[7,2,0,0$^{3,8}$]-undec-2-ene-2-carboxylate.

84 Sodium-(4S,8S,9R,10S,12R)-4-[4"-(N-succimidyl)phenylaminocarbonylamino]-10-(1'-hydroxyethyl)-11-oxo-1-azatricyclo[7,2,0,0$^{3,8}$]-undec-2-ene-2-carboxylate.

85 Sodium-(4S,8S,9R,10S,12R)-4-[(2"-chloropyrid-3"-yl-aminocarbonyl)amino]-10-(1'-hydroxyethyl)-11-oxo-1-azatricyclo[7,2,0,0$^{3,8}$]-undec-2-ene-2-carboxylate.

86 Sodium-(4S,8S,9R,10S,12R)-4-[(3",4"-dimethyl-1",2"oxazolyl-5-methylaminocarbonyl)amino]-10-(1'-hydroxyethyl)-11-oxo-1-azatricyclo[7.2.0.0$^{3.8}$]-undec-2-ene-2-carboxylate 87 Sodium-(4S,8S,9R,10S,12R)-4-(aminocarbonylamino)-10-(1'-hydroxyethyl)-11-oxo-1-azatricyclo[7.2.0.0$^{3.8}$]-undec-2-ene-2-carboxylate 88 Sodium-(4S,8S,9R,10S,12R)-4-[(dimethylaminoethylaminocarbonyl)aminocarbonyl)amino]-10-(1'-hydroxyethyl)-11-oxo-1-azatricyclo[7,2,0,0$^{3,8}$]-undec-2-ene-2-carboxylate.

89 Sodium-(4S,8S,9R,10S,12R)-4-[(4"-fluoro-3"-chlorobenzylaminocarbonyl)amino]-10-(1'-hydroxyethyl)-11-oxo-1-azatricyclo[7,2,0,0$^{3,8}$]-undec-2-ene-2-carboxylate.

90 Sodium-(4S,8S,9R,10S,12R)-4-[(propargylaminocarbonyl)amino]-10-(1'-hydroxyethyl)-11-oxo-1-azatricyclo[7,2,0,0$^{3,8}$]-undec-2-ene-2-carboxylate.

91 Sodium-(4S,8S,9R,10S,12R)-4-[(allylaminocarbonyl)amino]-10-(1'-hydroxyethyl)-11-oxo-1-azatricyclo[7,2,0,0$^{3,8}$]-undec-2-ene-2-carboxylate.

| Example | Starting Int. No | Material WT (g) | solvent volume ml | isocyanate R₂NCO R₂ | time | yield (mg) | IR cm-1 | H-NMR |
|---|---|---|---|---|---|---|---|---|
| 22 | 19 | 0.250 | acetone 30 ml | 4-trifluoromethyl phenyl | 2 hrs | 62 | 1749 | 7.32(d) 3.97(dd) 3.24 (dd) |
| 23 | 19 | 0.150 | acetone 18 ml | 4-methylphenyl | 1 hr | 45 | 1757 | 7.04(m) 3.98(dd) 3.23(dd) |
| 24 | 19 | 0.100 | acetone 15 ml | 4-nitrophenyl | 30 min | 30 | 1751 | 8.04(d) 3.97(dd) 3.24(dd) |
| 25 | 19 | 0.100 | acetone 15 ml | 4-chlorophenyl | 40 min | 25 | 1751 | 7.20(d) 3.97(dd) 3.23(dd) |
| 26 | 19 | 0.190 | acetone 15 ml | 3-nitrophenyl | 20 min | 30 | 1768 | 7.78(d) 3.97(dd) 3.24(dd) |
| 27 | 19 | 0.100 | CH3CN 12 ml | 4-dimethylamino sulphonylphenyl | 40 min | 85 | 1755 | 7.58(d) 3.96 (dd) 3.22(dd) |
| 28 | 19 | 0.100 | CH3CN 12 ml | 2-dimethylamino carbonylphenyl | 45 min | 51 | 1749 | 7.33(m) 3.99 (dd) 3.22(dd) |
| 29 | 19 | 0.100 | acetone 15 ml | 2-chlorophenyl | 30 min | 72 | 1755 | 7.17(td) 4.00 (dd) 3.23(dd) |
| 30 | 19 | 0.100 | acetone 15 ml | 3-trifluoromethyl phenyl | 1 hr | 22 | 1753 | 7.53(s) 3.97 (dd) 3.21(dd) |
| 31 | 19 | 0.100 | acetone 15 ml | 2-trifluoromethyl phenyl | 1 hr | 47 | 1752 | 7.58(m) 3.99 (dd) 3.21(dd) |
| 32 | 19 | 0.100 | CH3CN 12 ml | 4-trifluoromethyl pyrid-3-yl | 30 min | 50 | 1755 | 7.61(d) 4.01 (dd) 3.23(dd) |
| 33 | 19 | 0.100 | CH3CN 12 ml | 3-dimethylamino sulphonylphenyl | 45 min | 30 | 1755 | 7.67(s) 3.95 (dd) 3.21(dd) |
| 34 | 19 | 0.100 | CH3CN 14 ml | 1,3-dimethyl uracil-5-yl | 2 hrs | 70 | 1751 | 7.59(s) 3.99 (dd) 3.22(dd) |
| 35 | 19 | 0.100 | CH3CN 12 ml | 2-methylsulphonyl-oxy phenyl | 25 min | 70 | 1749 | 3.20(s) 4.02 (dd) 3.25(dd) |
| 36 | 19 | 0.100 | CH3CN 15 ml | N-methyl-2-oxo pyrid-5-yl | 4 hrs | 39 | 1751 | 6.45(d) 3.97 (dd) 3.23(dd) |
| 37 | 19 | 0.1 | acetone 15 ml | cyclohexyl | 6 h | 35 | 1751 | 3.21(dd), 3.95(dd), 3.24(m) |
| 38 | 19 | 0.11 | acetone 15 ml | 3-furyl | 15' | 79 | 1749 | 3.21(dd), 3.94(dd), 7.45(d) |
| 39 | 19 | 0.1 | acetone 4 ml H2O 2 ml | cyclopropyl | 1 h | 18 | 1749 | 3.2(dd), 3.93(dd), 2.29(m) |
| 40 (a) | 19 | 0.14 | MeCN 15 ml | 3-(N-methylpyridinium) methyl | 15' | 87 | 1755 | 3.23(dd), 3.95(dd), 8.49(d) |
| 41 | 19 | 0.1 | acetone 10 ml | 1-methyl-1H-pyrrol-2-yl | 1 h 15' | 33 | 1757 | 3.2–3.3(dd)1 4.00(dd), 3.24(s) |
| 42 | 19 | 0.13 | acetone 10 ml | 4-chlorobenzyl | 1 h 30' | 61 | 1755 | 3.14(dd), 3.78(dd), 4.24(d) |
| 43 | 19 | 0.1 | acetone 10 ml | 2-phenylethyl | 2 h | 32 | 1755 | 3.11(dd), 3.77(dd), 7.17(m) |
| 44 | 19 | 0.13 | MeCN 15 ml | 2-furyl | 30' | 57 | 1751 | 3.23(dd), 3.99(dd), 7.12(m) |
| 45 | 19 | 0.13 | MeCN 15 ml | 3-thiophenyl | 30' | 44 | 1749 | 3.19(dd), 3.93(dd), 7.18(dd) |
| 46 | 19 | 0.13 | MeCN 15 ml | 2-thiophenyl | 1 h | 50 | 1751 | 3.20(dd), 3.93(dd), 6.47(m) |
| 47 | 19 | 0.13 | MeCN 15 ml | 2-methyl-thiophen-5-yl | 45' | 71 | 1751 | 3.16(dd), 3.82(dd), 6.7(m) |
| 48 | 19 | 0.065 | MeCN 10 ml | 2-phenyl-pyridin-5-yl | 50' | 47 | 1751 | 3.23(dd), 3.97(dd), 8.37(d) |
| 49 | 19 | 0.1 | MeCN 10 ml | 3-Bromo-pyridin-5-yl | 30' | 61 | 1751 | 3.23(dd), 3.96(dd), 8.26(d) |
| 50 | 19 | 0.1 | MeCN 10 ml | 2,3-Dichloro- | 30' | 54 | 1751 | 3.26(dd), |

-continued

| Example | Starting Int. No | Material WT (g) | solvent volume ml | isocyanate $R_2NCO$ $R_2$ | time | yield (mg) | IR cm-1 | H-NMR |
|---|---|---|---|---|---|---|---|---|
| | | | | pyridin-5-yl | | | | 3.99(dd), 8.12(d) |
| 51 | 19 | 0.1 | MeCN 15 ml | 2-Chloro-pyridin5-yl | 30' | 58 | 1755 | 3.27(dd), 3.99(dd), 7.69(dd) |
| 52 | 19 | 0.1 | MeCN 15 ml | 4-methyl-1,2,3-thiadiazol-5-yl | 40' | 42 | 1751 | 3.22(dd), 3.95(dd), 2.39(s) |
| 53 | 19 | 0.11 | MeCN 15 ml | 1,2,3-thiadiazol-4-yl | 1 h | 60 | 1751 | 3.22(dd), 3.97(dd), 8.44(s) |
| 54 | 20 | 0.09 | water: acetone (1:1) 6 ml | 2-phenylethyl | 30' | 55 | 1747 | 3.07(dd), 3.42(m), 7.0–7.25(m) |
| 55 | 20 | 0.1 | water: acetone (1:1) 8 ml | 4-chlorobenzyl | 30' | 75 | 1747 | 3.07(m), 7.02(d), 7.12(d) |
| 56 | 20 | 0.1 | water: acetone (1:1) 6 ml | 2-phenoxyethyl | 30' | 60 | 1745 | 3.04(dd), 6.92(m), 7.23(m) |
| 57 (a) | 20 | 0.1 | acetone 5 ml | 3-picolyl | 2 h | 64 | 1745 | 3.10(d), 7.48(d), 8.2(m) |
| 58 | 20 | 0.1 | water: acetone (1:1) 6 ml | ethoxycarbonyl-methyl | 30' | 78 | 1781 | 1.09(t,), 3.18(dd), 3.64–3.75(AB) |
| 59 | 20 | 0.1 | water: acetone (1:1) 6 ml | 2-trimethylsilyl oxyethyl | 1 h | 60 | 1745 | 3.08(m), 3.17(dd), 3.89(t) |
| 60 | 19 | 0.12 | acetone 15 ml | 2-chloroethyl | 1 h | 66 | 1755 | 3.15(m), 3.19(dd), 3.40(m) |
| 61 | 19 | 0.1 | water: acetone (1:1) 8 ml | 2-trimethylsilyl oxyethyl | 1 h | 70 | 1744 | 3.10(dd), 3.23(dd), 3.44(m) |
| 62 | 19 | 0.1 | water: acetone (1:1) 8 ml | 5-ethoxycarbonyl pentyl | 1 h | 90 | 1734 | 2.19(t), 2.8–2.9(m), 3.14(dd) |
| 63 (a) | 19 | 0.12 | MeCN 10 ml | trimethyl-ammonium-ethyl | 30' | 72 | 1745 | 3.05(m), 3.06(s), 3.44–3.66(m) |
| 64 | 19 | 0.2 | water: acetone (1:1) 12 ml | 2-azidoethyl | 1 h | 160 | 1745 | 3.15(m), 3.21(m), 3.36(m) |
| 65 | 20 | 0.09 | water: acetone (1:1) 4 ml | 4-N-formylpiperidinyl | 1 h | 63 | 1749 | 5.1(m), 3.88 (dd), 3.15(m) |
| 66 | 20 | 0.1 | water: acetone (1:1) 5 ml | tetrahydropyran-4-yl | 1.5 h | 90 | 1749 | 3.88(dd), 3.1 (dd), 2.87(s) |
| 67 | 20 | 0.1 | water: acetone (1:1) 6 ml | N-allyloxycarbonyl piperidin-4-yl | 6 h | 80 | 1747 | 3.88(dd), 3.13 (dd), 2.88(s) |
| 68 | 20 | 0.125 | THF/H2O (9:1) 4 ml | cycohexyl | 30' | 45 | 1750 | 3.89(dd), 3.15(dd), 1.2–0.8(m) |
| 69 | 20 | 0.125 | THF/H2O (1:1) 4 ml | benzyl | 45' | 110 | 1740 | 3.71(dd), 3.11(dd), 7.24–7.07(m) |
| 70 | 20 | 0.125 | THF/H2O (1:1) 4 ml | ethyl | 30' | 15 | 1749 | 3.92(dd), 3.18(dd), 0.86(t) |
| 71 | 20 | 0.1 | Acetone/H2O (1:1) 4 ml | t-butyl | 30' | 12 | 1753 | 3.91(dd), 3.17(dd), 1.08(s) |
| 72 | 20 | 0.1 | toluene/H2O (1:1) 4 ml | cyclopropyl | 1 h | 17 | 1749 | 3.88(dd), 3.16(dd), 0.48(m) |
| 73 | 19 | 0.1 | acetone 40 | 4-aminosulphonyl benzyl | 3 | 42 | 1752 | 4.39(d) 3.83(dd) 3.16(dd) |
| 74 | 19 | 0.1 | acetone 30 | 2-methoxycarbonyl phenyl | 1 | 33 | 1759 | 3.74(s) 3.24(dd) 1.12(d) |
| 75 | 19 | 0.1 | acetone 15 | 2-isopropyl-phenyl | 1 | 65 | 1755 | 3.99(dd) 3.22(dd) 1.11(d) |
| 76 | 19 | 0.1 | acetone 12 | 4-bromophenyl | 1 | 79 | 1751 | 3.97(dd) 3.23(dd) 1.12(d) |
| 77 | 19 | 0.105 | acetone 15 | 3-chloro-4-fluoro-phenyl | 1.5 | 52 | 1755 | 3.97(m) 3.23(m) 111(d) |
| 78 | 19 | 0.069 | THF 6 | 4-methoxyphenyl | 3 | 10 | 1750 | 3.98(dd) |

-continued

| Example | Starting Int. No | Material WT (g) | solvent volume ml | isocyanate $R_2NCO$ $R_2$ | time | yield (mg) | IR cm-1 | H-NMR |
|---|---|---|---|---|---|---|---|---|
| 79 | 19 | 0.06 | acetone 7 | 3,4,5-trimethoxy phenyl | n.d. | 27 | 1752 | 3.24(dd) 1.12(d) 3.68(s) 3.59(s) |
| 80 | 19 | 0.1 | acetone 15 | 2-nitrophenyl | 3 | 28 | 1718 | 3.23(dd) 3.99(dd) 3.22(dd) |
| 81 | 19 | 0.1 | acetone 15 | 3-methylthio phenyl | 1 | 75 | 1755 | 1.10(d) 3.21(dd) 2.31(s, 3H) |
| 82 | 19 | 0.1 | CH3CN 15 | 2-methylsulphonyl phenyl | 0.75 | 66 | 1747 | 1.09(d) 3.99(dd) 3.24(dd) 3.04(s) |
| 83 | 19 | 0.1 | CH3CN 25.6 | 2-methylsulphinyl phenyl | 4 | 17 | n.d. | 3.30(dd) 2.73(s) 1.16(d) |
| 84 | 19 | 0.1 | CH3CN 25 | 4-N-succinimdoyl phenyl | 1.5 | 87 | 1755 | 3.95(dd) 3.21(dd) 2.77(m) |
| 85 | 19 | 0.1 | CH3CN 25.6 | 2-chloro-pyrid-3-yl-5-methyl | 0.75 | 90 | 1751 | 3.99(dd) 3.23(dd) 1.10(d, 3H) |
| 86 | 19 | 0.1 | acetone 30 | 3,4,-dimethyl 1,2-oxazolyl-5-methyl | 1.5 | 7 | n.d. | 3.16(dd) 2.17(s) 2.00(s) |
| 87 | 19 | 0.2 | acetone 30 | trimethylsilyl | n.d. | 20 | n.d. | 3.95(dd) 3.20(dd) 1.10(d) |
| 88 | 19 | 0.1 | acetone 20 | dimethylamino-ethyl | 7 | 15 | 1751 | 3.94(dd) 3.23(dd) 2.71(s) |
| (a) 89 | 19 | 0.11 | acetone 20 ml | 4-fluoro-3-chloro benzyl | 1.5 | 88 | 1751 | 4.26(d), 3.86(dd), 3.15(dd) |
| (a) 90 | 19 | 0.15 | acetone 20 ml | propargyl | 2 | 105 | 1753 | 3.95(dd), 3.20(dd), 2.37(t) |
| (a) 91 | 19 | 0.1 | acetone 20 ml | allyl | 2 | 40 | 1750 | 5.96(d), 3.94(dd), 3.21(dd) |

(a) In this process the amine $R_2NH_2$ and carbonyldimidazole were used in place of isocyanate $R_2NCO$.

PHARMACY EXAMPLES

Tablets

|  | mg/tab |
|---|---|
| Compound of Example 1 | 320 |
| Lactose | 150 |
| Ethyl cellulose | 20 |
| Sodium lauryl sulphate | 7 |
| Magnesium stearate | 3 |
| Tablet core | 500 mg |

The active ingredient and the lactose are blended together and then granulated using water as the granulating fluid. The dried granules are blended with the ethyl cellulose, sodium lauryl sulphate and magnesium stearate and the tablet core formed using an appropriate punch. The tablet may then be coated using conventional techniques and coatings.

Example B

|  | mg/tab |
|---|---|
| Compound of Example 1 | 320 |
| Compressible sugar | 170 |
| Sodium lauryl sulphate | 7 |
| Magnesium stearate | 3 |
| Tablet core | 500 |

The active ingredient and the excipients are blended together and then compressed using an appropriate punch. If required the tablet thus formed may be coated in a conventional manner.

Granules

|  | mg/unit dose |
|---|---|
| Compound of Example 1 | 320 |
| Starch 100 |  |
| Cellulose | 40 |
| Polymethacrylate | 30 |
| Sodium lauryl sulphate | 7 |
| Magnesium stearate | 3 |
| Flavouring agent | qs |

A solution of the active ingredient in ethanol is sprayed into a suitable fluid bed granulator charged with the major excipients. The granules so formed are dried and screened. If desired the granules may then be coated with a suitable enteric coating and dried. The dried granules are then blended with the remaining excipients including any flavouring agent and coated, for example with an enteric coating. The granules thus obtained may be filled into capsules or the like for a single dose presentation or filled into bottles for subsequent preparation of a multi dose oral liquid presentation.

Dry Powder for Injection

| active ingredient (Compound of Example 1) | 538 mg per vial. |
|---|---|

Fill sterile vials with the sterile active ingredient. Purge the vial head space with sterile nitrogen; close the vials using rubber plugs and metal overseals (applied by crimping). The product may be constituted by dissolving in Water for Injection (10 ml) or other suitable sterile vehicle for injection shortly before administration.

The antibacterial activity of the compounds of the invention may be readily determined using conventional test procedures. For example the antibacterial activity of the compounds of the invention was determined using a standard microtiter broth serial dilution test. In this test the broth was incubated with approximately $10^5$ colony forming units of the test organism and incubated at 35° for 18 hours in the presence of test compound. Results obtained using the rest procedure are given in the table below and are expressed as minimum inhibitory concentrations (MIC) in micrograms/ml.

Example No's

| Organism | 1 | 10 | 12 | 13 | 9 | 21 |
|---|---|---|---|---|---|---|
| S Aureus 663E | 0.5 | 0.25 | 0.5 | 0.5 | 0.25 | 0.1 |
| F Faecalis B5OE | 2 | 1 | 2 | 2 | 1 | 8 |
| E Coli TEMI | 0.25 | 0.12 | <0.1 | 0.25 | 0.12 | 0.1 |
| E Cloacae | 4 | 2 | 2 | 2 | 0.5 | 0.5 |
| C Prefringens | <0.01 | 0.12 | <0.1 | 0.12 | 0.12 | 0.1 |
| B Fragilis | 0.25 | 0.5 | 0.25 | 0.50 | 0.50 | 0.1 |

The compounds of the invention are essentially non toxic at therapeutically useful doses. For example no adverse effects were observed when compounds of the invention were administered to mice at therapeutically useful dose levels.

We claim:

1. A compound of general formula (I)

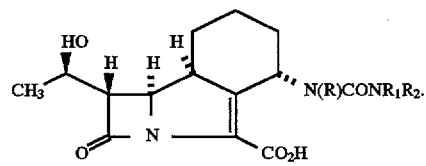

(I)

salts and metabolically labile esters thereof;

wherein R represents hydrogen or $C_{1-6}$alkyl;

$R_1$ represents hydrogen or $C_{1-6}$alkyl;

$R_2$ represents hydrogen or an optionally substituted, alkyl, alkenyl, alkynyl, aryl, cycloalkyl or heterocyclic group.

2. Compounds as claimed in claim 1, wherein R represents hydrogen or methyl.

3. Compounds as claimed in claims 1 or 2 when $R_1$ represents hydrogen or methyl.

4. Compounds as claimed in any of claims 1 to 3 wherein $R_2$ represents hydrogen, methyl, ethyl, t-butyl, allyl, propargyl, azidoethyl, hydroxyethyl, chloroethyl, dimethylaminoethyl, trimethylammonium-ethyl, 1-carboxyethyl, 2-ethoxycarbonylethyl, phenoxyethyl, benzamidomethyl, t butyxycarbonylaminomethyl, benzyl (optionally substituted by chloro and or fluoro, or by aminosulphonyl), phenylethyl, pyridylmethyl, pyridylethyl, N-methylpyridinium-methyl, 1,2 oxazolylmethyl, furfuryl, pyridyl, N-methylpyridinium, pyridyl (substituted by 1 or 2 chlorine or bromine atoms, trifluoromethyl, phenyl, or methoxy), N-methyl-2-pyridone, furyl, 2-methylfuryl, thienyl, methylthienyl, N-methylpyrrole, thiadiazolyl, methylthiadiazolyl, uracilyl, N-methyluracilyl, N,N-dimethyluracilyl, cyclohexyl, cyclopropyl, or 4-tetrahydropyranyl, or N-substituted 4-piperidinyl.

5. Compounds as claimed in any of claims 1 to 4 wherein at least one of R, $R_1$ or $R_2$ is other than hydrogen.

6. Compounds as claimed in any of claims 1 to 5 wherein $R_2$ represents phenyl (optionally substituted by hydroxy, methoxy, cyano, acetamido or methylsulphonyl), pyridyl, pyridylmethyl, phenoxyethyl, furfuryl or uracilyl.

7. Compounds as claimed in any of claims 1 to 6 having the following configuration

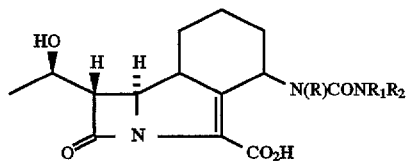

8. The compounds (4S,8S,9R,10S,12R)-4-(phenylaminocarbonylamino)-10-(1'-hydroxyethyl)-11-oxo-1-azatricyclo[7.2.0.0$^{3,8}$]-undec-2-ene-2-carboxylic acid;

(4S,8S,9R,10S,12R)-4-(3"-pyridineaminocarbonylamino)-10-(1'-hydroxyethyl)-11-oxo-1-azatricyclo[7.2.0.0$^{3,8}$]-undec-2-ene-2-carboxylic acid;

(4S,8S,9R,10S,12R)-4-[(2"-hydroxyphenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(4"-methylsuphonylphenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-(uracil-5'-amino)carbonylamino-10-(1'-hydroxyethyl)-11-oxo-1-aza-tricyclo [7.2.0.0$^{3,8}$]-undec-2-ene carboxylic acid;

(4S,8S,9R,10S,12R)-4-(3"-picolylaminocarbonylamino)-10-(1'-hydroxyethyl)-11-oxo-1-azatricyclo[7.2.0.0$^{3,8}$]-undec-2-ene-2-carboxylic acid;

(4S,8S,9R,10S,12R)-4-(2"-furfurylaminocarbonylamino)-10-(1'-hydroxyethyl)-11-oxo-1-azatricyclo[7.2.0.0$^{3,8}$]-undec-2-ene-2-carboxylic acid;

(4S,8S,9R,10S,12R)-4-[(2"-methoxyphenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(benzylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(3"-cyanophenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(2"-phenoxyethylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(4"-acetamidophenylaminocarbonyl)amino]-10-(1'-hydroxyethyl)-11-oxo-1-azatricyclo[7,2,0,0$^{3,8}$]-undec-2-ene-2-carboxylic acid;

(4S,8S,9R,10S,12R)-4-[(4"-cyanophenylaminocarbonyl) amino]-10-(1'-hydroxyethyl)-11-oxo-1-azatricyclo[7,2,0, 0$^{3,8}$]-undec-2-ene-2-carboxylic acid;

and physiologically acceptable salts and metabolically labile esters thereof.

9. A pharmaceutical composition comprising a compound as claimed in any of claims 1 to 8 in admixture with one or more physiologically acceptable carriers or excipients.

10. A method of treatment of a human or non human body to combat bacterial infections comprising administration to said body of an effective amount of a compound as claimed in any of claims 1 to 8.

11. A method as claimed in claim 10 wherein the bacterial infections are systemic.

12. A method as claimed in claim 10 wherein the bacterial infections are topical.

13. A pharmaceutical composition comprising a compound as claimed in claim 8 in admixture with one or more physiologically acceptable carriers or excipients.

14. A method of treatment of a human or non-human animal body to combat bacterial infections comprising administration to said body of an effective amount of a compound as claimed in claim 8.

15. A method as claimed in claim 14 wherein the bacterial infections are systemic.

16. A method as claimed in claim 14 wherein the bacterial infections are topical.

* * * * *